(12) United States Patent
Franzen et al.

(10) Patent No.: US 7,829,275 B2
(45) Date of Patent: Nov. 9, 2010

(54) LIGHT ADDRESSABLE ELECTROCHEMICAL DETECTION OF DUPLEX STRUCTURES

(75) Inventors: Stefan Franzen, Apex, NC (US); Daniel L. Feldheim, Cary, NC (US)

(73) Assignee: North Carolina State University, Raleigh, NC (US)

( * ) Notice: Subject to any disclaimer, the term of this patent is extended or adjusted under 35 U.S.C. 154(b) by 663 days.

(21) Appl. No.: 10/236,205

(22) Filed: Sep. 6, 2002

(65) Prior Publication Data

US 2003/0143581 A1 Jul. 31, 2003

Related U.S. Application Data

(63) Continuation of application No. PCT/US02/23174, filed on Jul. 22, 2002.

(60) Provisional application No. 60/307,019, filed on Jul. 20, 2001.

(51) Int. Cl.
 *C12Q 1/68* (2006.01)
(52) U.S. Cl. .......................................................... 435/6
(58) Field of Classification Search .................... 435/6, 435/91.2
 See application file for complete search history.

(56) References Cited

U.S. PATENT DOCUMENTS

| | | | |
|---|---|---|---|
| 3,607,691 A | 9/1971 | Goldberg et al. | |
| 4,851,331 A | 7/1989 | Vary et al. | |
| 5,082,627 A | 1/1992 | Stanbro | |
| 5,185,243 A | 2/1993 | Ullman et al. | |
| 5,200,313 A | 4/1993 | Carrico | |
| 5,277,782 A | 1/1994 | DuPree et al. | |
| 5,412,087 A * | 5/1995 | McGall et al. ............ | 536/24.3 |
| 5,420,419 A | 5/1995 | Wood | |
| 5,472,881 A | 12/1995 | Beebe et al. | |
| 5,483,068 A | 1/1996 | Moulton et al. | |
| 5,489,776 A | 2/1996 | Lung | |
| 5,503,728 A | 4/1996 | Kaneko et al. | |
| 5,503,980 A | 4/1996 | Cantor | |
| 5,528,035 A | 6/1996 | Masarik | |
| 5,573,907 A | 11/1996 | Carrino et al. | |
| 5,669,979 A * | 9/1997 | Elliott et al. ................... | 134/1 |
| 5,679,524 A | 10/1997 | Nikiforov et al. | |
| 5,770,369 A | 6/1998 | Meade et al. | |
| 5,866,336 A | 2/1999 | Nazarenko et al. ............. | 435/6 |
| 5,874,046 A * | 2/1999 | Megerle ..................... | 422/68.1 |
| 5,922,537 A * | 7/1999 | Ewart et al. ..................... | 435/6 |
| 5,952,172 A | 9/1999 | Meade et al. | |
| 6,004,755 A | 12/1999 | Wang | |
| 6,027,893 A | 2/2000 | Orum et al. | |
| 6,046,038 A | 4/2000 | Nilsen | |
| 6,051,378 A | 4/2000 | Monforte et al. | |
| 6,063,573 A | 5/2000 | Kayyem | |
| 6,066,457 A | 5/2000 | Hampson et al. | |
| 6,090,933 A | 7/2000 | Kayyem et al. | |
| 6,127,127 A | 10/2000 | Eckhardt et al. | |
| 6,144,031 A | 11/2000 | Herring et al. | |
| 6,171,793 B1 | 1/2001 | Phillips et al. | |
| 6,203,989 B1 | 3/2001 | Goldberg et al. | |
| 6,265,155 B1 | 7/2001 | Meade et al. | |
| 6,291,188 B1 | 9/2001 | Meade et al. | |
| 6,301,038 B1 | 10/2001 | Fitzmaurice et al. | |
| 6,355,491 B1 | 3/2002 | Zhou et al. | |
| 6,361,944 B1 * | 3/2002 | Mirkin et al. ................... | 435/6 |
| 6,361,994 B1 * | 3/2002 | Hudson et al. ............. | 435/325 |
| 6,403,317 B1 | 6/2002 | Anderson | |
| 6,503,711 B1 | 1/2003 | Krull et al. | |
| 6,506,564 B1 | 1/2003 | Mirkin et al. | |
| 6,541,617 B1 | 4/2003 | Bamdad et al. | |
| 6,589,737 B1 | 7/2003 | Gruber et al. | |
| 6,589,742 B2 | 7/2003 | Edman et al. | |

(Continued)

FOREIGN PATENT DOCUMENTS

WO WO94/21820 9/1994

(Continued)

OTHER PUBLICATIONS

Willner et al. ("Photoelectrochemistry with Controlled DNA-Cross-Linked CdS Nanoparticle Arrays" Agnew Chem Int Ed Engl. May 18, 2001. 40(10), pp. 1861-1864).*

(Continued)

Primary Examiner—Christopher M. Babic
(74) Attorney, Agent, or Firm—Jenkins, Wilson, Taylor & Hunt, P.A.

(57) ABSTRACT

A method of detecting the presence of an analyte, such as a target nucleic acid sequence, protein sequence or small molecule, which can also be employed to detect the formation of duplex structures, is disclosed. The method can comprise nucleic acids, proteins and small molecules, employing photoelectrochemically active nanoparticles, branched polymers or other structures that carry photoelectrochemically active molecules capable of generating a photocurrent when excited by light in the presence of an electric field is disclosed. The method can be employed to detect hybridization on an array and can be employed in sequencing, mutational analysis (for example, single nucleotide polymorphisms and other variations in a population) and for monitoring gene expression by analysis of the level of expression of messenger RNA extracted from a cell. The method is applicable to the detection of antibody binding or other protein binding for analyte detection in an array format. The creation of an array addressable by light is disclosed.

23 Claims, 20 Drawing Sheets

U.S. PATENT DOCUMENTS

| | | | |
|---|---|---|---|
| 2002/0094526 | A1 | 7/2002 | Bayley et al. |
| 2002/0103517 | A1 | 8/2002 | West et al. |
| 2002/0119455 | A1 | 8/2002 | Chan |
| 2002/0127574 | A1 | 9/2002 | Mirkin et al. |
| 2002/0160195 | A1 | 10/2002 | Halas et al. |
| 2003/0003300 | A1 | 1/2003 | Korgel et al. |
| 2003/0034486 | A1 | 2/2003 | Korgel |
| 2003/0044805 | A1 | 3/2003 | Mirkin et al. |
| 2003/0077625 | A1 | 4/2003 | Hutchison |
| 2004/0053222 | A1 | 3/2004 | Storhoff et al. |
| 2004/0180369 | A1 | 9/2004 | Franzen et al. |
| 2005/0191651 | A1 | 9/2005 | Franzen et al. |
| 2006/0094860 | A1 | 5/2006 | Take |
| 2006/0099146 | A1 | 5/2006 | Chow et al. |
| 2006/0099148 | A1 | 5/2006 | Fisher et al. |
| 2006/0286570 | A1 | 12/2006 | Rowlen et al. |
| 2007/0009954 | A1 | 1/2007 | Wang et al. |
| 2007/0031829 | A1 | 2/2007 | Yasuno et al. |
| 2007/0042400 | A1 | 2/2007 | Choi et al. |
| 2007/0042419 | A1 | 2/2007 | Barany et al. |
| 2010/0000881 | A1 | 1/2010 | Franzen et al. |

FOREIGN PATENT DOCUMENTS

| | | |
|---|---|---|
| WO | WO96/41011 | 12/1996 |
| WO | WO97/31256 | 8/1997 |
| WO | WO98/04740 | 2/1998 |
| WO | WO 98/39352 | 9/1998 |
| WO | WO99/51778 | 10/1999 |
| WO | WO 01/00876 A1 | 6/2000 |
| WO | WO03/062783 | 1/2003 |
| WO | WO2005/042785 | 5/2005 |

OTHER PUBLICATIONS

Drouard et al. ("CdS nanoparticle-modified electrodes for photoelectrochemical studies" Chemical Communications. 1999. pp. 67-68).*

Steel et al. ("Electrochemical Quantitation of DNA Immobilized on Gold" Analytical Chemistry. 1998. vol. 70, No. 22: pp. 4670-4677).*

Drouard et al. ("CdS nanoparticle-modified electrodes for photoelectrochemical studies" Chemical Communications. 1999. pp. 67-68).*

Steel et al. ("Electrochemical Quantitation of DNA Immobilized on Gold" Analytical Chemistry. 1998. vol. 70, No. 22: pp. 4670-4677).*

Drouard et al. ("CdS nanoparticle-modified electrodes for photoelectrochemical studies" Chemical Communications. 1999. pp. 67-68).*

Steel et al. ("Electrochemical Quantitation of DNA Immobilized on Gold" Analytical Chemistry. 1998. vol. 70, No. 22: pp. 4670-4677).*

Microarray Biochip Technology, (entire book) 2000.

Microarrays and Related Technologies: Miniaturation and Acceleration of Genomic Research, Report 8, May 2001 *Cambridge Healthtech Institute's Genomic Reports Series*.

Duggan et al., *Expression profiling using cDNA microarrays, Nature Genomics* 21:10-14 (Jan. 1999).

Cheung etal., *Making and reading microarrays, Nature Genomics* 21:15-19 (Jan. 1999).

Lipshutz et al., *High density synthetic oligonucleotide arrays, Nature Genomics* 21:20-24 (Jan. 1999).

Bowtell, *Options available—from start to finish—for obtaining expression data by microarray, Nature Genomics* 21:25-32 (Jan. 1999).

Brown, et al., *Exploring the new world of the genome with DNA microarrays, Nature Genomics* 21:33-37 (Jan. 1999).

Cole et al., *The genetics of cancer—a 3D model, Nature Genomics* 21:38-41 (Jan. 1999).

Hacia, *Resequencing and mutational analysis using oligonucleotide microarrays, Nature Genomics* 21: 42-47 (Jan. 1999).

Debouck et al., *DNA microarrays in drug discovery and development, Nature Genomics* 21:48-50 (Jan. 1999).

Bassett, Jr., et al., *Gene expression informatics-it's all in your mine, Nature Genomics* 21:51-55 (Jan. 1999).

Chakravarti, *Population genetics-making sense out of sequence, Nature Genomics* 21:56-60 (Jan. 1999).

Nuovo et al., *In Situ Amplication Using Universal Energy Transfer-labeled Primers, The J. Of Histochemistry & Cytochemistry* 47(3):273-279 (1999).

Pastinen et al., *Multiplex, fluorescent, solid-phase minisequencing for efficient screening of DNA sequence variation, Clinical Chemistry* 42(9):1391-1397(1996).

Dubiley et al., *Fractionation, phosphorylation and ligation on oligonucleotide microchips to enhance sequencing by hybridization, Nucleic Acids Research* 27(12):2259-2265 (1997).

Michael, et al., *Randomly Ordered Addressable High-Density Optical Sensor Arrays, Anal. Chem.* 70:1242-1248 (1998).

Walt, *Fiber Optic Imaging Sensors, Acc. Chem. Res.* 31:267-278 (1998).

Lockhart, et al., *Expression monitoring by hybridization to high-density oligonucleotide arrays, Nature Biotechnology* 14:1675-1684 (Dec. 1996).

Pirrung, *Spatially Addressable Combinatorial Libraries, Chem. Rev.* 97:473-488 (1997).

Yershov et al., *DNA analysis and diagnostics on oligonucleotide microchips, Proc. Natl. Acad. Sci. USA* 93:4913-4918 (May 1996).

Taton et al., *Scanometric DNA Array Detection with Nanoparticle Probes, Science* 289:1757-1760 (Sep. 8, 2000).

Singh-Gasson et al., *Maskless fabrication of light-directed oligonuleotide microarrays using a digital micromirror array, Nature Biotechnology* 17-974-978 (Oct. 1999).

Beier et al., *Production by quantitative photolighograhic synthesis of individiually quality checked DNA microarrays, Nucleic Acids Research* 28(4):i-vi (2000).

Written Opinion from corresponding PCT patent application, PCT Appl. No. PCT/US02/23174.

Notification of Transmittal of International Preliminary Examination Report for PCT Appl. No. PCT/US02/23174 dated Sep. 2, 2004.

Ferguson et al., *A fiber-optic DNA biosensor microarray for the analysis of gene expression. Nature Biotechnology*. vol. 14 pp. 1681-1684 (1996).

Jones, C.D., and Lyon, L.A., *Photothermal Patterning of Microgel/Gold Nanoparticle Composite Colloidal Crystals. Journal of the American Chemical Society*. vol. 125, No. 2 pp. 460-465 (2003).

Kai et al., *Detection of PCR products of Escherichia coli O157:H7 in human stool samples using surface plasmon resonance(SPR). FEMS Immunology and Medical Microbiology*. vol. 29, No. 4 pp. 283-288 (2000).

Link et al., *Laser-Induced Shape Changes of Colloidal Gold Nanorods Using Femtosecond and Nanosecond Laser Pulses. Journal of Physical Chemistry B* vol. 104 No. 26 pp. 6152-6163 (2000).

Lowe et al., *Laser-induced Temperature Jump Electrochemistry on Gold Nanoparticle-Coated Electrodes. Journal of the American Chemical Society*. vol. 125, No. 47 pp. 14258-14259 (2003).

Notification Concerning Transmittal of International Preliminary Report on Patentability (Chapter I of the Patent Cooperation Treaty) corresponding to International Application No. PCT/US2004/036426 dated May 11, 2006.

Notification of Transmittal of the International Preliminary Report on Patentability corresponding to PCT Application No. PCT/US2004/036178 dated May 11, 2006.

Notification of Transmittal of the International Search Report and the Written Opinion of the International Searching Authority, or the Declaration for PCT/US2004/036178 dated Feb. 21, 2005.

Notification of Transmittal of the International Search Report and the Written Opinion of the International Searching Authority, or the Declaration for PCT/US2004/036426 dated Mar. 23, 2005.

Official Action corresponding to U.S. Appl. No. 10/759,496 dated Jul. 26, 2006.

Official Action corresponding to U.S. Appl. No. 10/759,496 dated Mar. 12, 2007.

Official Action corresponding to U.S. Appl.No. 10/759,496 dated Sep. 18, 2007.

Official Action corresponding to U.S. Appl. No. 10/759,496 dated Feb. 26, 2008.

Official Action corresponding to U.S. Appl. No. 10/759,496 dated Nov. 12, 2008.
Official Action corresponding to U.S. Appl. No. 10/759,496 dated Jun. 22, 2009.
Official Action corresponding to U.S. Appl. No. 10/978,678 dated Oct. 13, 2006.
Official Action corresponding to U.S. Appl. No. 10/978,678 dated May 25, 2007.
Official Action corresponding to U.S. Appl. No. 10/978,678 dated Aug. 11, 2008.
Official Action corresponding to U.S. Appl. No. 10/978,678 dated Apr. 29, 2009.
Official Action corresponding to U.S. Appl. No. 10/978,678 dated Sep. 9, 2009.
Official Action corresponding to U.S. Appl. No. 10/978,678 dated Nov. 12, 2009.
Official Action corresponding to U.S. Appl. No. 10/978,756 dated Feb. 27, 2007.
Official Action corresponding to U.S. Appl. No. 10/978,756 dated Nov. 27, 2007.
Official Action corresponding to U.S. Appl. No. 10/978,756 dated Mar. 19, 2009.
Park, So-Jung et al., *Array-Based Electrical Detection of DNA with Nanoparticles Probes. Science.* vol. 295 pp. 1503-1506 (2002).
Sershen, S.R. et al., *Temperature-Sensitive Polymer-Nanoshell Composites for Photothermally Modulated Drug Delivery. Journal of Biomedical Materials Research.* vol. 51 pp. 293-298 (2000).
Stewart, *Making and Using DNA microarrays: A short course at Cold Spring Harbor Laboratory. Genome Research.* vol. 10 pp. 1-3 (2000).
Subramanian et al., *Semiconductor-Metal Composite Nanostructures. To What Extent Do Metal Nanoparticles Improve the Photocatalytic Activity of TiO Films? The Journal of Physical Chemistry B.* vol. 105, No. 46 pp. 11439-11446 (2001).
Written Opinion of the International Searching Authority corresponding to International Patent Application No. PCT/US2004/036178 dated May 11, 2006.
Written Opinion of the International Searching Authority corresponding to International Patent Application No. PCT/US2004/036426 dated May 11, 2006.
Zhang et al., *Reconstruction of DNA sequencing by hybridization. Bioinformatics.* vol. 19, No. 1 pp. 14-21 (2003).
Beydoun, D et al., "Role of nanoparticles in photocatalysis," Journal of Nanoparticle Research. vol. 1 pp. 439-458 (1999).
Hashimoto et al., "Sequence specific gene detection with a gold electrode modified with DNA probes and an electrochemically active dye," Analytical Chemistry. vol. 66 pp. 3830-3833 (1994).
Lahav et al., "Photoelectrochemistry with Integrated Photosensitizer-Electron Acceptor and Au-Nanoparticle Arrays." Journal of the American Chemical Society. vol. 122 pp. 11480-11487 (2000).
Logunov et al., "Electron Dynamics of Passivated Gold Nanocrystals Probed by Subpicosecond Transient Absorption Spectroscopy." The Journal of Physical Chemistry B. vol. 101, No. 19 pp. 3713-3719 (1997).
Notification of Transmittal of the International Search Report or the Declaration corresponding to International Patent Application No. PCT/US02/23174 dated Sep. 2, 2003.
Official Action corresponding to U.S. Appl. No. 10/978,756 dated Dec. 31, 2009.
Ramalho, J.F., and Rosch, R., "Synthesis of Modified Oligonucleotides." Access to Nucleic Acid Chemistry. pp. 1-35 (2000).
Skrabanek, L., and Campagne, F., "TissueInfo: high-throughput identification of tissue expression profiles and specificity," Nucleic Acids Research. vol. 29, No. 21 pp. 1-8 (2001).
Slides from presentation entitled New Physical Methods for Genomic and Proteomic Analysis. Stefan Franzen. North Carolina State University. Raleigh, North Carolina, pp. 1-30.
Slides from presentation entitled "Thermographic Detection of Nucleic Acids," presentation by Marc L. Sauthier dated Aug. 26, 2004; Raleigh, North Carolina, pp. 1-30.
Slides from presentation entitled "Thermographic Detection of Nucleic Acids," presentation by Marc L. Sauthier dated Jun. 10, 2003; Raleigh, North Carolina, pp. 1-47.
Yamada et al., "A photoresponsive molecular assembly consisting of ruthenium(II) tris(2,2'-bipyridine)-viologen linked disulfide and hexadecanethiol prepared on a gold surface: effect of viologen moiety." Journal of Electoanalytical Chemistry. vol. 426 pp. 23-26 (1997).
Zhu et al., "Global Analysis of Protein Activities Using Proteome Chips." Science. vol. 293 pp. 2101-2105 (2001).
Alvarez et al., "Optical Absorption Spectra of Nanocrystal Gold Molecules," J. Phys. Chem. B. vol. 101 pp. 3706-3712 (1997).
Bulyk et al., "Quantifying DNA-Protein interactions by double-stranded DNA Arrays," Nature Biotechnology. vol. 17 pp. 573-577 (1999).
Chee et al., "Accessing Genetic Information with High-Density DNA Arrays," Science. vol. 274, No. 5287 pp. 610-614 (1996).
Chen, S., and Huang, K., "Electrochemical and Spectroscopic Studies of Nitrophenyl Moieties Immobilized on Gold Nanoparticles," Langmuir. vol. 16, No. 4, pp. 2014-2016 (2000).
Elghanian et al., "Selective Colorimetric Detection of Polynucleotides Based on the Distance-Dependent Optical Properties of Gold Nanoparticles," Science. vol. 277, No. 5329 pp. 1078-1081 (1997).
Enüstün, B.V., and Turkevich, J., "Coagulation of Colloidal Gold," Physical and Inorganic Chemisty. vol. 85, No. 21 pp. 3317-3328 (1963).
Gilles et al., "Single nucleotide polymorphic discrimination by an electronic dot blot assay on semiconductor microships," Nature Biotechnology. vol. 17 pp. 365-370 (1999).
Gould et al., "Efficiencies of Photoinduced Electron-Transfer Reactions: Role of the Marcus Inverted Region in Return Electron Transfer within Geminate Radical-Ion Pairs," Journal of the American Chemical Society. vol. 112 pp. 4290-4301 (1990).
Halushka et al., "Patterns of single-nucleotide polymorphisms in candidate genes for blood-pressure homeostasis," Nature Genetics. vol. 22 pp. 239-247 (1999).
Koide et al., "Effects of spacer-chain length on the photoelectrochemical responses of monolayer assemblies with rutherium tris(2,2'-bipyridine)—viologen linked disulfides," Thin Solid Films. vol. 350 pp. 223-227 (1999).
Landegren et al., "A Ligase-Mediated Gene Detection Technique," Science. vol. 241, No. 4869 pp. 1077-1080 (1988).
Lander, "Array of Hope," Nature Genomics. vol. 21 pp. 3-9 (1999).
Marinakos et al., "Gold Nanoparticles as Templates for the Synthesis of Hollow Nanometer-Sized Conductive Polymer Capules," Advanced Materials. vol. 11, No. 1 pp. 34-37 (1999).
Marinakos et al., "Template Synthesis of One-Dimensional Au, Au-Poly(pyrrole), and Poly(pyrrole) Nanoparticle Arrays," Chemical Materials. vol. 10 pp. 1214-1219 (1998).
Nickerson et al., "Automated DNA diagnostics using an ELISA-based oligonucleotide ligation assay," PNAS. vol. 87 pp. 8923-8927 (1990).
Schena et al., "Quantitative Monitoring of Gene Expression Patterns with a Complementary DNA Microarray," Science, vol. 270, No. 5235 pp. 467-470 (1995).
Storhoff, J.J., and Mirkin, C.A., "Programmed Materials Synthesis with DNA, " Chemical Reviews, vol. 99 pp. 1849-1862 (1999).
Storhoff et al., "One-Pot Colorimetric Differentiation of Polynucleotides with Single Base Imperfections Using Gold Nanoparticle Probes," Journal of the American Chemical Society. vol. 120 pp. 1959-1984 (1998).
Swanson et al., "A fully multiplexed CMOS biochip for DNA analysis," Sensors and Actuators B. vol. 64 pp. 22-30 (2000).
Tender et al., "Cyclic Voltammetric Analysis of Ferrocene Alkanethiol Monolayer Electrode Kinetics Based on Marcus Theory," Anal. Chem. vol. 66 pp. 3173-3181(1994).
Uosaki et al., "Electrochemical Characteristics of a Gold Electrode Modified with a Self-Assembled Monolayer of Ferrocenylalkanethiols," Langmuir. vol. 7 pp. 1510-1514 (1991).
Zu, Y., and Bard, A.J., "Electrogenerated Chemiluminescence. 67. Dependence of Light Emission of the Tris(2,2') bipyridylruthenium(II)/Tripropylamine System on Electrode Surface Hydrophobicity." Analytical Chemistry. vol. 73 pp. 3960-3964 (2001).

* cited by examiner

LIGHT ADDRESSABLE ELECTROCHEMICAL DETECTION OF DUPLEX STRUCTURES

CROSS REFERENCE TO RELATED APPLICATIONS

The present patent application is a continuation of PCT International Patent Application No. PCT/US02/23174 filed Jul. 22, 2002, which claims priority to U.S. Provisional Patent Application Ser. No. 60/307,019 entitled "LIGHT ADDRESSABLE ELECTROCHEMICAL DETECTION OF DUPLEX STRUCTURES", which was filed Jul. 20, 2001 and is incorporated herein by reference.

TECHNICAL FIELD

The present invention relates to the detection of duplexes using photoelectrochemistry.

| Abbreviations | |
|---|---|
| ATP | adenosine triphosphate |
| ADP | adenosine diphosphate |
| bipy | bipyridine |
| BSPP | bis(p-sulfonatophenyl)phenylphosphine |
| cDNA | complementary DNA |
| DNA | deoxyribonucleic acid |
| EDTA | ethylenediaminetetraacetic acid |
| HDPE | high density polyethylene |
| HEPES | N-2-hydroxyethylpiperazine-N'-2-ethanesulfonic acid |
| ITO | indium tin oxide |
| kDa | kilodalton(s) |
| MES | 2-[N-morpholino]ethanesulfonic acid |
| mRNA | messenger RNA |
| NDP | nucleotide diphosphate |
| nm | nanometer |
| nt | nucleotide |
| NTP | nucleotide triphosphate |
| OLA | oligonucleotide ligation assay |
| PAGE | polyacrylamide gel electrophoresis |
| PCR | polymerase chain reaction |
| PEC | photoelectrochemical |
| PEG | polyethylene glycol |
| Ph | phenyl |
| pI | isoelectric point |
| RNA | ribonucleic acid |
| SDS | sodium dodecyl sulfate |
| SDS-PAGE | sodium dodecyl sulfate polyacrylamide gel electrophoresis |
| ssDNA | single stranded DNA |
| STM | scanning tunneling microscopy |
| TEA | triethylamine |
| TEOA | triethanolamine |
| TPA | tripropylamine |

| Amino Acid Abbreviations | | |
|---|---|---|
| Single-Letter Code | Three-Letter Code | Name |
| A | Ala | Alanine |
| V | Val | Valine |
| L | Leu | Leucine |
| I | Ile | Isoleucine |
| P | Pro | Proline |
| F | Phe | Phenylalanine |
| W | Trp | Tryptophan |
| M | Met | Methionine |
| G | Gly | Glycine |
| S | Ser | Serine |
| T | Thr | Threonine |
| C | Cys | Cysteine |
| Y | Tyr | Tyrosine |
| N | Asn | Asparagine |
| Q | Gln | Glutamine |
| D | Asp | Aspartic Acid |
| E | Glu | Glutamic Acid |
| K | Lys | Lysine |
| R | Arg | Arginine |
| H | His | Histidine |

BACKGROUND ART

A variety of techniques have been developed to analyze nucleic acids, proteins (e.g. receptors), and other biological analytes for the presence of interactions, mutations, or other characteristics of interests. Such techniques can be used to determine, for example, if a patient has a particular disease or has a predisposition toward the disease. That is, nucleic acid-based analysis can be used to verify the presence or absence of expressed genes or polymorphisms. Nucleic acid-based and other analysis can also be used to monitor progression of disease, assess effectiveness of therapy or to modify dosage formulations. Protein binding assays can be used to test for specific proteins in blood or cell extracts. Antibody binding assays can be used to detect a number of analytes including small molecules and proteins.

One technique for analyzing biological analytes employs a microarray (or microelectronics biochip) that generates a hybridization pattern representative of binding characteristics of a target analyte within the sample or a pattern of binding events on a protein or antibody array (see, e.g., Schena (ed.), (2000) *Microarray Biochip Technology*, Eaton Publishing, Natick, Mass.; Vrana et al., (2001) "Microarrays and Related Technologies: Miniaturization and Acceleration of Genomic Research", Cambridge Healthtech Institute Report 8, May 2001). In one example, a nucleic acid microarray can include a rectangular array of immobilized single stranded nucleic acid fragments. Each element within the array includes a few tens to millions of copies of identical single stranded strips of nucleic acid containing specific sequences of nucleotide bases. Identical or different fragments of a nucleic acid can be provided at each different element of the array. For example, in a rectangular microarray, location (1,1) can contain a different single stranded fragment of a nucleic acid than location (1,2), which can also differ from location (1,3), and so on. See, e.g., Schena (ed.), (2000) *Microarray Biochip Technology*, Eaton Publishing, Natick, Mass.; Pirrung, (1997) *Chem. Rev.* 97: 473-486.

Generally, microarrays typically employ fluorescence or electrical phenomenology to indicate a positive detectable result. In one method that employs fluorescence imaging, a double stranded nucleic acid sample to be analyzed is first separated into individual single stranded sequences and then fragmented into smaller probes. Alternatively, single stranded sequences can be synthesized in a DNA synthesizer. Each probe is then tagged with a fluorescent molecule. The probes are applied to the microarray, at which point each probe binds only with complementary nucleic acid fragments embedded on the microarray. Probes that are not complementary to any of the elements of the microarray will not bind to the microarray and can be discarded during subsequent fluidic reactions and washes. Thus, only those nucleic acid samples in the microarray that contain fragments that bind complementary sequences of the probe nucleic acid sample will hybridize with probes containing fluorescent molecules. Typically, a fluorescent light source is then applied to the microarray to generate a fluorescent image identifying which elements of the microarray bind to the patient's nucleic acid sample and which do not. The image is then analyzed to determine which specific nucleic acid fragments were present in the original sample and an assessment is then made as to whether a particular disease, mutation or other condition is present in the patient sample.

By way of specific example, a particular element of the microarray can be exposed to fluorescently-labeled fragments of DNA representative of a particular type of cancer. If that element of the array fluoresces under fluorescent illumination, it is known that the DNA of the sample contains the DNA sequence indicative of that particular type of cancer. Hence, a conclusion can be drawn that the patient providing the sample is already afflicted with that particular type of cancer or, alternatively, is possibly predisposed towards that cancer. By providing a wide variety of known DNA fragments on the microarray, the resulting fluorescent image can be analyzed to identify a wide range of conditions.

The detection of interactions on solid surfaces has been used for a variety of applications, including the identification of infectious organisms in clinical specimens (Spargo et al., (1993), *Mol. Cell. Probe* 7: 395-404; Martin, (1994) in *The Polymerase Chain Reaction* (Mullis, Ferre & Gibbs, eds.), pp. 406-17. Berkhauser, Boston), the quantitation of mRNA for gene expression analysis (Schena et al., (1995) *Science* 270: 467-70), and the sequencing or resequencing of genomic DNA on high-density "chip" arrays (Chee et al., (1996) *Science* 274: 610-13).

As noted, one embodiment of DNA microarray technology involves the attachment of a fluorescent label to a probe nucleic acid sequence, which is allowed to hybridize with a DNA sequence bound to a surface. Duplex formation is detected after removing the unhybridized DNA from the solid surface. Detection of fluorescently emitted photons is required to indicate the formation of a hybridization duplex and, therefore, analysis of high-density arrays labeled in this manner can require high-resolution fluorescence microscopes. Alternatively, indirect detection of hybridization can be accomplished using sandwich assays where the surface-bound hybrid is subsequently hybridized to an additional signal probe that carries one or more fluorescent labels or enzymes that impart fluorescent capability to a non-fluorescent substrate. Spargo et al., (1993) *Mol. Cell. Probe* 7: 395-404. In another embodiment, melting profiles can be examined in lieu of the more common fluorescent approach (Taton et al., (2000) *Science* 289:1757-1760).

The use of DNA hybridization arrays ("DNA microarrays") has also had an impact on the technology available for sequencing cDNA, for sequencing mRNA and for determining the expression levels of selected genes. Stewart, (2000) *Genome Res.* 10:1-3; Yershov et al., (1996) *Proc. Natl. Acad. Sci. U.S.A.* 93:4913-4918; Lockhart et al., (1996) *Nature Biotechnol.* 14: 1675-1680; Ferguson et al., (1996) *Nature Biotechnol.* 14: 1680-1684. While this technology does not necessarily compete with current DNA sequencing methodology, it is very useful for rapid determination of the DNA content of mRNA expression level in a cell. Bulyk et al., (1999) *Nat. Biotechnol.* 6: 573-7; Lockhart & Winzeler, (2000) *Nature* 405: 827-36; Eisen & Brown, (1999) *Method Enzymol.* 303: 179-205. Reverse transcription of mRNA in reaction mixtures that comprise fluorescently labeled nucleotide triphosphates (NTPS) provides cDNA oligomers that can subsequently be hybridized to a surface. Thus, these microarrays are useful for genomic analysis in the laboratory and are of increasing importance in medical applications. Halushka et al., (1999) *Nat. Genet.* 22: 239-47; Rockett & Dix, (1999) *Environ. Health Persp.* 107: 681-85.

Efficient and rapid detection of mRNA expression levels has become particularly relevant, because mRNA analysis can allow a researcher or clinician to arrive at a conclusion or diagnosis based on an understanding of observed changes in protein expression. While DNA microarray technology is currently used predominantly as a tool for research, it has the potential to play a valuable role as a diagnostic tool.

The currently available detection strategy for DNA hybridization on surface arrays employs fluorescently labeled oligonucleotides and a reader consisting of a fluorescence microscope. Lipschutz et al., (1999) *Nature Genet* 21: 20-24. Currently, the most compact array is the GeneChip™ array that consists of 65,536 single stranded DNA sequences on a chip. Lipschutz et al., (1999) *Nat. Genet. Sup.* 21: 20-24; Harrington et al., (2000) *Curr. Opin. Microbiol.* 3: 285-91. Hybridization is probed by determining the fluorescence intensity at the location of each individual sequence of the DNA array. In the ideal case only complementary DNA in solution will hybridize and produce a fluorescent signal. However, non-specific binding and single/multi-base mismatches can provide a significant background signal. Although the background intensity is often weaker for non-specific interactions, the interpretation of the hybridization assay in terms of sequence becomes much more difficult. Consequently, statistical analysis is often required to extract the appropriate sequence information.

Protein and antibody arrays have also been developed that employ similar principles, but do not employ photocurrent-based detection methods. In protein and antibody arrays, binding of an analyte permits detection of a target protein. Relative quantities of material or binding constants can also be determined depending on the experimental configuration. However, in these methods detection of binding is usually based a fluorescence measurement. This requires fluorescent labeling of the target analyte, which can be undesirable.

A number of technological barriers have inhibited the employment of microchip and microarray technology in routine diagnostic and other applications. For example, the labeling of probe and/or target DNA with fluorescent moieties requires a cumbersome procedure and expensive detection apparatus is required for the detection of the labeled probe. Additionally, problems with false positive signals typically associated with the read-out of chip-based hybridization assay have been an obstacle. Moreover, hardware requirements have limited the use of microarrays useful for screening large numbers of samples. These and other problems are solved in whole or in part by the present invention.

SUMMARY OF THE INVENTION

A method of detecting a target analyte is disclosed. In one embodiment, the method comprises: (a) providing a conductive support comprising a target analyte attached thereto, the target analyte further comprising a nanoparticle comprising a photoelectrochemically active moiety; (b) exposing the photoelectrochemically active moiety to light, thereby generating a photoelectric current between the photoelectrochemically active moiety and the conductive support; and (c) measuring the photoelectric current, as an indication of the presence or the amount of the target analyte on the conductive support.

The method can employ a single electrode and can achieve detection at each target analyte attachment point on the electrode by detecting current flow following irradiation of each target analyte attachment point by a light source, for example a laser beam.

In the above non-limiting embodiments of the present invention, a nanoparticle can comprise a material selected from the group consisting of a metal, a metal oxide, a ceramic, a dendrimer, a semiconductor and an organic polymer. Optionally, the nanoparticle can comprise a material selected from the group consisting of titanium, titanium dioxide, tin, tin oxide, silicon, silicon dioxide, iron, iron$^{III}$ oxide, silver, gold, copper, nickel, aluminum, steel, indium, indium tin oxide, fluoride-doped tin, ruthenium oxide, germanium cadmium selenide, cadmium sulfide and titanium alloy. In one embodiment, the support comprises a conductive material.

Optionally, the probe moiety is selected from the group consisting of single stranded DNA oligomer, a single stranded RNA oligomer, a peptide nucleic acid analog, double stranded DNA, a small molecule, an antibody, a polypeptide, a peptide, a synthesized target analyte, a target analyte isolated from a cell, a target analyte that is reverse transcribed from a nucleic acid sequence, a target analyte comprising intact genomic DNA, a target analyte comprising fragmented genomic DNA, mRNA, a PCR product and an OLA product. In one embodiment, the probe moiety is bound to the support in an addressable array. In another embodiment, the photoelectrochemically active moiety comprises a ruthenium center. Light sources can comprise, for example, a tungsten halogen light source, a xenon arc lamp or a laser. In yet another embodiment, the exposing is by rastering and the exposing and the detecting are performed simultaneously.

Optionally, the disclosed non-limiting embodiments of the present invention can further comprise passivating the support with a passivation moiety before contacting the target moiety associated with the support with the nanoparticle under hybridization conditions. Further, the disclosed non-limiting embodiments of the present invention can further comprise contacting the support with a secondary component after contacting the target associated with the support with the nanoparticle under hybridization conditions. A secondary component can comprise, for example, a photoelectrochemically active moiety.

It is therefore an object of the present invention to provide a novel method of detecting a duplex. This object is achieved in whole or in part by the present invention.

An object of the invention having been stated hereinabove, other objects will be evident as the description proceeds, when taken in connection with the accompanying Drawings and Examples as best described hereinbelow.

BRIEF DESCRIPTION OF THE DRAWINGS

In FIG. 1A, ferrocene is shown to be associated with a gold or TiO$_2$ nanoparticle, which is tethered to a gold surface by a nucleic acid duplex linker.

In FIG. 1B, Ru(bipy)$_3$$^{2+}$ is shown to be associated with a TiO$_2$ nanoparticle, which is tethered to an indium tin oxide (ITO) electrode by a nucleic acid duplex linker.

DETAILED DESCRIPTION OF THE INVENTION

Figure 1A:
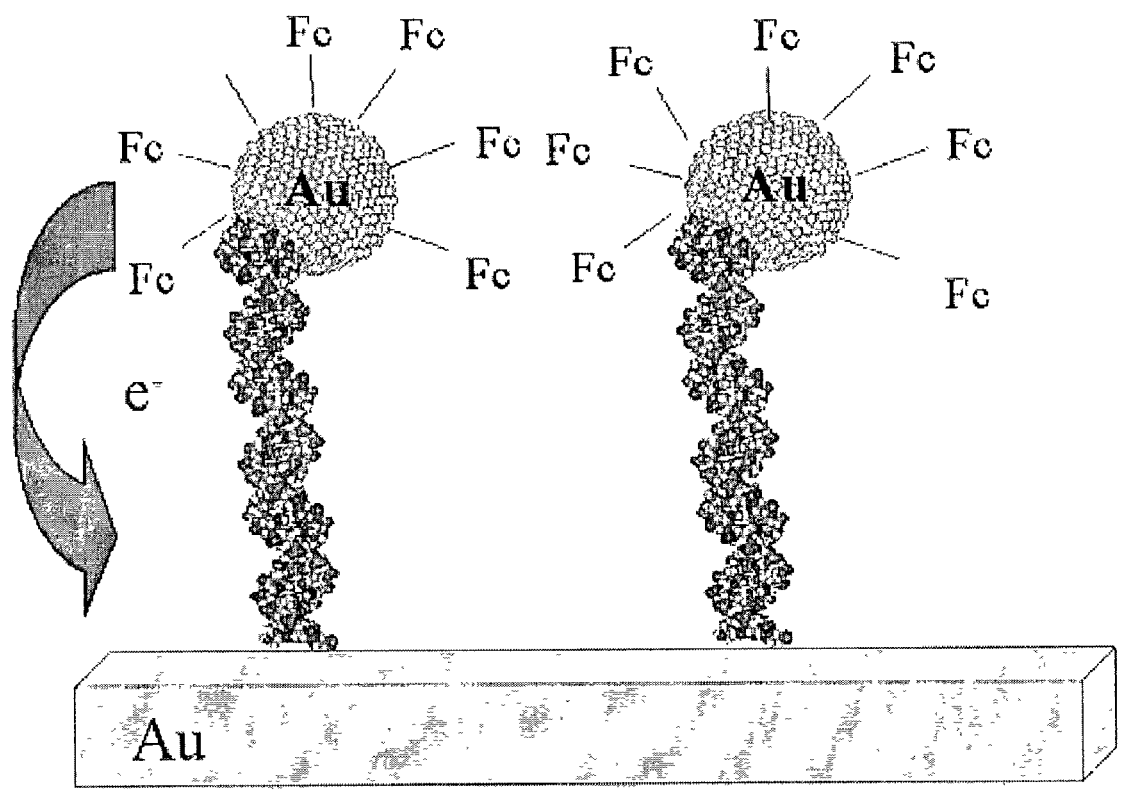
FIG. 1A is a diagram depicting an electrochemical detection strategy employing DNA-nanoparticle conjugates to carry redox molecules in accordance with the present invention.

A method of detecting the formation of duplex structures is disclosed. In one embodiment, the method employs photoelectrochemically active nanoparticles, branched polymers or other structures that carry photoelectrochemically active molecules capable of generating a photocurrent when excited by light in the presence of an electric field. An aspect of this method is the creation of an array addressable by light rather than an electronic microarray structure. Another aspect of the invention includes combining the photoelectrochemical reactions of a variety of semi-conductor and doped semi-conductor materials in a conjugate with a target analyte for the purpose of detecting hybridization at the surface of an electrode. The method can be employed to detect hybridization on an array and can be employed, for example, in sequencing, in mutational analysis (single nucleotide polymorphisms and other variations in a population), for monitoring gene expression by analysis of the level of expression of messenger RNA extracted from a cell, for detecting an interaction between two or more proteins and detecting an interaction between a protein and a nucleic acid and detecting an interaction between a nucleotide sequence and a structure comprising two or more nucleotide sequences (e.g. a duplex), to name just a few applications of the present invention. The method can complement or even supplant fluorescent or electrochemical detection of hybridization. By employing light to photoexcite a sample, a photocurrent can be generated. The current can then be detected and/or compared with an amount of current that can be generated by a single redox probe or even a collection of redox probes bound to the probe oligonucleotide strand. A colloidal system such as a nanoparticle or branched dendrimer or other polymeric structure, facilitates detection by providing one or more photoelectrochemically active redox sites capable of photoinduced electron transfer to the substrate. In one embodiment, reduction of a redox mediator can occur when redox probes are solvent exposed.

In one aspect, the present invention broadly discloses nanoparticle technology useful, for example, in screening a plurality of immobilized nucleic acid or protein samples for hybridization between an immobilized nucleic acid probe and a target analyte, for example a nanoparticle-nucleic acid target or a nanoparticle-protein target. Specific aspects of the present invention described hereinbelow include the attachment of a nucleic acid oligomer to a nanoparticle; the design of an electrode support; the attachment of a nucleic acid oligomer to the electrode support; and the characterization of duplexes formed between immobilized DNA and target-nanoparticle complexes and between immobilized proteins and target-nanoparticle complexes.

The nanoparticles employed in accordance with the present invention also provide a useful alternative to fluorescence for quantifying surface hybridization. There are a number of features that help to avoid false positives due to non-specific binding. For example, the nanoparticles provide an electrostatic handle for the application of electric fields to the surface that can permit discrimination of mismatches at much lower applied voltages. Additionally, it has been demonstrated that the use of nanoparticles can provide a unique label for detection by either optical or electrochemical techniques. In one aspect of the present invention, intermolecular interactions can be identified by the detection of a photocurrent. The detection of a photocurrent represents an advance beyond prior art methods of identifying intermolecular interactions, which typically rely on fluorescence-based detection techniques. This flexibility, combined with the use of intermolecular interactions demonstrates that nanoparticles can be used to provide a superior type of DNA array, in accordance with the present invention.

Additionally, the use of microarrays allows a higher density of target analytes to be bound to the support surface. Thus, a microarray can be designed that reflects the spatial requirements of the sample itself. In other words, a consideration in microarray design can be the space required for a sample to be attached to a support plus the space required to prevent interaction between adjacent samples, which can lead to a high volume of array members.

Nanoparticles offer advantages over the application of electric fields to surface-attached double stranded DNA, which has been used to discriminate between single-base mismatch and complete complementarity. For example, in many prior art surface-attached double stranded DNA approaches, single stranded DNA is driven off in the electric field, in an effort to eliminate non-specifically bound fluorescently labeled oligomers. Gilles et al., (1999) *Nature Biotechnol.* 17: 365-70; Heller et al., (2000) *Electrophoresis* 21: 157-64. However, the voltages required to deliver this effect are high, making the practical application of this technique limited. In the present invention, on the other hand, the use of nanoparticles offers an advantage over prior art methods employing electric fields, since the surface charge on the nanoparticles can be controlled and augmented to levels that are higher than the charge densities along the phosphodiester backbone of DNA. The voltage required to drive off non-specifically bound and mismatched DNAs can thus be explored and controlled as a function of the surface charge density of the bound nanoparticle.

Another advantage of the methods and compositions of the present invention is the ability to address a microarray by light and to thereby generate a detectable photocurrent. Light sources that can be employed in the methods of the present invention can include, for example, a xenon arc lamps and a laser, among other light sources. As described further hereinbelow, in one aspect of the present invention laser beams and other light sources can be employed to address individual cells or locations on a microarray, which will then generate a photocurrent, the presence of which is indicative of intermolecular interactions.

I. Definitions

Following long-standing patent law convention, the terms "a" and "an" mean "one or more" when used in this application, including the claims.

As used herein, the terms "addressable array" and "array" are used interchangeably and mean a collection of entities arranged on a support in a manner such that each entity occupies a unique and identifiable position.

As used herein, the term "attach," and grammatical derivatives thereof, means any association of one moiety with one or more other moieties. The association can take any form for example via a covalent bond, via hybridization, via non-covalent interactions, such as receptor-ligand interactions.

As used herein, the term "amino acid sequence" means an oligopeptide, peptide, polypeptide, or protein sequence, and fragments thereof, and naturally occurring or synthetic molecules. As used herein, the term "amino acid sequence" refers to the amino acid sequence of a synthetic peptide or a naturally occurring protein molecule, amino acid sequence, and the like; the term is not meant to limit the amino acid sequence to the complete, native amino acid sequence associated with a given protein molecule.

As used herein, the term "chemical modification" and grammatical derivations thereof means alteration of a first moiety by covalently or ionically binding a second moiety to the first moiety. Chemical modification can involve the addition of a detectable moiety to a peptide or protein. Chemical modification can also refer to the catalyzed or uncatalyzed addition of a phosphate group to a peptide.

As used herein, the term "detect" and grammatical derivations thereof means confirming the presence of a target entity by observing the occurrence of a detectable signal, such as an electrical, radiologic or spectroscopic signal that will appear exclusively in the presence of the target entity.

As used herein, the terms "duplex", "duplex structure" and "hybridization duplex" are used interchangeably and mean a structure formed of at least two different members. Duplexes can comprise two or more DNA sequences, RNA sequences or proteins. Duplexes can form via hybridization of complementary strands of DNA or RNA or by any other association mechanism. The members of a duplex can associate with each other covalently, noncovalently, ionically or by any other mechanism. A member of a duplex can itself comprise one, two or more members. Thus a duplex can comprise a structure comprising two members, one or both of which can be a duplex itself. For example, one member of a duplex can comprise a single stranded nucleic acid sequence (immobilized or in solution) and the second member of the duplex can comprise a nucleic acid double stranded duplex (immobilized or in solution), effectively making the duplex a triplex structure.

As used herein, the term "electrical current" means the movement of electrons from a higher energy level to a lower energy level. Generally, electrical current is the flow of electrical charge, and the term can also refer to the rate of charge flow through a circuit.

As used herein, when referring to a compound, the term "electroactive" means the compound has the ability to change electronic configuration. The term refers to a molecule or structure and includes the ability to transfer electrons, the ability to act as a conductor of electrons and the ability to act as an electron donor or acceptor. The term specifically encompasses the ability of a molecule to act as the donor in an electron transfer when it is photoexcited.

As used herein, the term "gene" is used for simplicity and means a functional protein, polypeptide or peptide encoding unit. As will be understood by those of ordinary skill in the art, this term includes both genomic sequences and cDNA sequences. Some embodiments of genomic and cDNA sequences are disclosed herein.

As used herein, the term "gold" means element 79, which has the chemical symbol Au; the term specifically excludes any connotation related to color or other colorimetric properties.

As used herein, the term "homology", and grammatical derivations thereof, means a degree of similarity. There can be partial homology or complete homology (i.e., identity). A partially complementary nucleic sequence that at least partially inhibits an identical sequence from hybridizing to a target nucleic acid is referred to using the functional term "substantially homologous." The inhibition of hybridization of the completely complementary sequence to the target sequence can be examined using a hybridization assay (Southern or northern blot, solution hybridization and the like) under conditions of low stringency. A substantially homologous sequence or hybridization probe can compete for and inhibit the binding of a completely homologous sequence to the target sequence under conditions of low stringency. Conditions of low stringency do not permit non-specific binding; low stringency conditions do, however, require that the binding of two sequences to one another be a specific (i.e., selective) interaction. The absence of non-specific binding can be tested by employing a second target sequence that lacks even a partial degree of similarity (e.g., less than about 30% identity). In the absence of non-specific binding, the probe will not hybridize to the second non-complementary target sequence.

As used herein, the term "hybridization", and grammatical derivations thereof, means the association of a first structure with a second structure. The term encompasses a first structure associated with two or more structures, which can be chemically similar or dissimilar to each other or the first structure. The first and second structures can comprise one, two or more molecules. There is no limitation on the mechanism of association and the term used broadly to specifically cover association by chemical, electrochemical, mechanical or other mechanism. The term "hybridization conditions", therefore, refers to conditions under which a hybridization event (i.e. an association) can occur. Hybridization conditions can vary with the chemical nature of the molecules involved and, although there are no restrictions on hybridization conditions, hybridization conditions can generally reflect known physiological conditions. Of course, the term "hybridization" also specifically includes hybridization between nucleic acids, as generally recognized in the art.

As used herein, the term "interact" and grammatical derivations thereof, means contact, exchange or association between two or more entities, such as can be detected using an assay based on observable properties, (e.g., an electrochemical assay). The term "interact" is also meant to include "binding" interactions between molecules. An Interaction can potentially occur between all numbers and types of entities, for example, an interaction can be nucleic acid-nucleic acid, protein-protein, protein-nucleic acid, protein-small molecule (e.g. receptor-ligand) in nature.

As used herein, the term "isolated," and grammatical derivations thereof, means oligonucleotides substantially free of other nucleic acids, proteins, lipids, carbohydrates or other materials with which they can be associated, such association being either in cellular material or in a synthesis medium. The term can also be applied to peptides and polypeptides (and fragments thereof), in which case the polypeptide is substantially free of nucleic acids, carbohydrates, lipids and other undesired polypeptides.

As used herein, the term "label", and grammatical derivations thereof, means the attachment of a first moiety, capable of detection by electrochemical, spectroscopic, radiologic or other detection method, to a second moiety.

As used herein the terms "microarray" and "array" are used interchangeably and generally mean an arrangement of molecules or groups of molecules on a support. Thus, the terms encompass arrangements comprising proteins, nucleic acids and groups thereof associated with a support.

As used herein, the term "modified", and grammatical derivations thereof, means an alteration from an entity's normally occurring state. An entity can be modified by removing discrete chemical units or by adding discrete chemical units. The term "modified" encompasses detectable labels as well as those entities added as aids in purification.

As used herein, the term "modulate", and grammatical derivations thereof, means an increase, decrease, or other alteration of any or all chemical and biological activities or properties mediated by a nucleic acid sequence or a peptide. The term "modulation" as used herein refers to both upregulation (i.e., activation or stimulation) and downregulation (i.e. inhibition or suppression) of a response by any mode of action.

As used herein, the term "monolayer" means a coating, for example on a surface, comprising extended elements having first and second ends and being bound to the surface, either directly or indirectly, by the first end. In a monolayer, the second end can be associated with other elements. The term "monolayer" specifically encompasses a substantially linear chemical structure comprising a linker bound to a support surface at one end, and to a sequence of nucleic acids at the other end. Monolayers can comprise, for example, single stranded nucleic acid sequences, nucleic acid duplexes, protein duplexes, protein-nucleic acid structures, structures comprising small molecules or any combination thereof. Monolayers can exist in solution without a surface. When a monolayer is of heterogeneous composition, the term "mixed monolayer" can be used to describe the monolayer. The terms "monolayer" and "mixed monolayer" can be used interchangeably to generally describe a monolayer.

As used herein, the term "mutation" carries its traditional connotation and means a change, inherited, naturally occurring or introduced, in a nucleic acid or polypeptide sequence, and is used in its sense as generally known to those of ordinary skill in the art.

As used herein, the terms "nano", "nanoscopic", "nanometer-sized", "nanostructured", "nanoscale", and grammatical derivatives thereof are used synonymously and in some cases interchangeably and mean nanoparticles, nanoparticle composites and hollow nanocapsules less than, for example, about 1000 nanometers (nm) in diameter, less than about 200 nanometers in diameter and less than about 100 nanometers in diameter. Although a nanoparticle can comprise any material, in one embodiment, a nanoparticle comprises an elemental metal, semiconductor material, polymeric material or a metal oxide. In other examples, a nanoparticle can comprise gold, titanium, $TiO_2$, tin, $SnO_2$, indium tin oxide (ITO), conductive metal oxides, conductive polymers or any other conductive substance. The terms can refer not only to the central component of a nanoparticle (i.e. a nanoparticle central component), but a composite comprising a metal and other components as well.

As used herein, the term "nanoparticle" means any structure comprising a nanoparticle central component. Thus, the term "nanoparticle" encompasses all structures comprising a nanoparticle central component and any other attached moiety or moieties, such as, but not limited to, a photoelectrochemically active moiety and a target analyte.

As used herein, the terms "nanoparticle central component" and "central component" are used interchangeably and mean a component to which a probe and/or a target analyte is bound. Typically, but not necessarily, a nanoparticle central component is an approximately spherical metal atom-comprising entity. In one example, a nanoparticle central component is a particle comprising a material such as a semiconductor, a metal, or a metal oxide. In other examples, a nanoparticle central component can comprise a polymeric species or any other conducting material.

As used herein, the terms "nucleic acid microarray" and "nucleic acid hybridization array" are used interchangeably and mean an arrangement of nucleic acid sequences bound to a support. In one example, nucleic acids sequences bound to a support are ordered such that each nucleic acid sequence has a unique, identifiable location on the support. A nucleic acid microarray can comprise a single stranded nucleic acid sequence or a double stranded nucleic acid sequence. In another example, a nucleic acid microarray can comprise a nucleic acid structure wherein a sequence comprises a sticky end (e.g. a structure comprising two or more nucleic acid sequences that are complementary to each other, however one sequence overhangs the other sequence and comprises a sequence of interest). In yet another example, a nucleic acid microarray can comprise a nucleic acid structure comprising two sequences of identical length (e.g. that form a blunt end). A nucleic acid microarray can comprise, for example, a nucleic acid sequence comprising cDNA.

As used herein, the terms "oligomer" and "oligo" are used interchangeably and mean a molecule comprising a plurality of discrete identifiable units. When the term refers to a nucleic acid sequence, oligomers can be of any length, although oligomers between 5 and 50 nucleotides (or base pairs if an oligomer is double stranded) in length are typical.

As used herein, the term "photoelectrochemically active", and grammatical derivations thereof, means having the ability to transfer or transport electrons following photoexcitation by light. Generally, the term refers to a chemical entity that can be promoted to an excited state by absorption of energy at a given wavelength and can act as an electron donor or acceptor.

As used herein, the term "photoelectrochemically active moiety" means any structure adapted to generate or carry an electric current generated in response to the application of light. For example, a photoelectrochemically active moiety can comprise a structure comprising a photoinducible electron donor, which, can act as a donor in a photoinduced electron transfer reaction; as a photoredox agent, which can act as the acceptor in a photoinduced electron transfer reaction; or as a sensitizer or mediator, which can act in a manner analogous to the role of a catalyst in a chemical reaction.

As used herein, the term "photoredox agent" means a compound capable of light-induced electron transfer. A representative, but non-limiting, list of photoredox agents includes ruthenium, iron, and osmium complexes comprising bipyridine, amine, imidazole, chloride, and methyl viologen.

As used herein, the term "polypeptide" means any polymer comprising any of the 20 protein amino acids, regardless of its size. Although "protein" is often used in reference to relatively large polypeptides, and "peptide" is often used in reference to small polypeptides, usage of these terms in the art overlaps and varies. The term "polypeptide," as used herein, refers to peptides, polypeptides and proteins, unless otherwise stated. As used herein, the terms "protein", "polypeptide" and "peptide" are used interchangeably herein when referring to a gene product.

As used herein, the terms "probe," "probe moiety," "probe sequence" and "probe oligomer" are used interchangeably and mean a moiety that forms one member of a duplex. For example, a probe can comprise a single or double stranded nucleic acid sequence, which can associate with a second single or double stranded nucleic acid sequence to form a triplex structure. Typically, a probe serves as an immobilized capture moiety. There is no requirement that the identity of a "probe," "probe moiety," "probe sequence" or a "probe oligomer" be known, and when it is desired to ascertain the identity of a "probe moiety," "probe sequence" or a "probe oligomer," such a determination can be made at any time, given the parameters of the design of an experiment. There is no limit on the composition of a "probe," "probe moiety," "probe sequence" or a "probe oligomer." A "probe," "probe moiety," "probe sequence" or a "probe oligomer" can be synthesized or isolated and can comprise modified nucleic acids and/or modified amino acids. A "probe moiety," "probe sequence" or a "probe oligomer" can be, for example, a nucleic acid duplex, a sequence of cDNA, a protein, or a small molecule.

As used herein, the terms "redox compound", "redox center", "redox group", "redox mediator" and "redox chromophore" are used interchangeably and mean a molecule or part of a molecule, a redox-active or photoactive nanoparticle that is capable of undergoing changes in its electronic properties.

As used herein, the term "secondary component" means any compound that is contacted with a target moiety bound to a support, following exposure of the target moiety bound to a support to a probe moiety. Secondary component can be any kind of compound, and the term specifically encompasses nanoparticles, as disclosed and described herein. Secondary components can include redox compounds, such as ferrocene, photoelectrochemically active compounds, such as ruthenium bypyridine, and fluorescent compounds, such as Texas red or Oregon green.

As used herein, the term "sequencing" means determining the ordered linear sequence of nucleic acids or amino acids of a DNA or peptide (or protein) target sample, using manual or automated laboratory techniques.

As used herein, the term "small molecule" means any molecule having a molecular weight of 5000 Daltons or less.

As used herein, the term "substantially pure" means a sample (e.g. a synthesized molecule, a polynucleotide or a polypeptide) that is substantially free of the sequences and molecules with which it is associated in its natural state, and those molecules used in the isolation procedure. In one embodiment, the term "substantially free" means that a sample is at least 50%, free of the materials and compounds with which is it associated in nature. In other embodiments, the term means that a sample is 70%, 80% or 90% free of the materials and compounds with which is it associated in nature.

As used herein, the terms "target analyte," "target moiety," "target sequence" and "target oligomer" are used interchangeably and mean a moiety that forms one member of a duplex pair. There is no requirement that the identity of a "target analyte," "target moiety," "target sequence" or a "target oligomer" be known, and when it is desired to ascertain the identity of a "target analyte," "target moiety," "target sequence" or a "target oligomer," such a determination can be made at any time, given the parameters of the design of an experiment. There is no limit on the composition of a "target analyte," "target moiety," "target sequence" or a "target oligomer." A "target analyte," "target moiety," "target sequence" or a "target oligomer" can be synthesized or isolated and can comprise modified nucleic acids and/or modified amino acids. A "target analyte," "target moiety," "target sequence" or a "target oligomer" can be, for example, a nucleic acid duplex, a sequence of cDNA or a protein.

As used herein, the term "peptide nucleic acid analog", abbreviated PNA, means a DNA analog wherein the backbone of the analog, for example a sugar backbone in DNA, is a pseudopeptide. A PNA backbone can comprise, for example, a sequence of repeated N-(2-amino-ethyl)-glycine units. A peptide nucleic acid analog reacts as DNA would react in a given environment, and can additionally bind complementary nucleic acid sequences and various proteins. Peptide nucleic acid analogs offer the potential advantage over unmodified DNA of the formation of stronger bonds, due to the neutrally charged peptide backbone of the analogs, and can impart a higher degree of specificity than is achievable by unmodified DNA.

II. General Considerations

In accordance with the present invention, analyte-nanoparticle conjugates can be employed in a novel method of on-chip detection of hybridization events. The nanoparticles and methods of the present invention can be applied to any array, including but not limited to nucleic acid arrays, such as those created by spotter technology or photolithography technology, although arrays ordered in various ways can also be prepared (see, e.g., Michael et al., (1998) *Anal. Chem.* 70:1242-1248, Cheung et al., (1999) *Nature Genet. Supplement* 21:15-19).

Figure 1B:
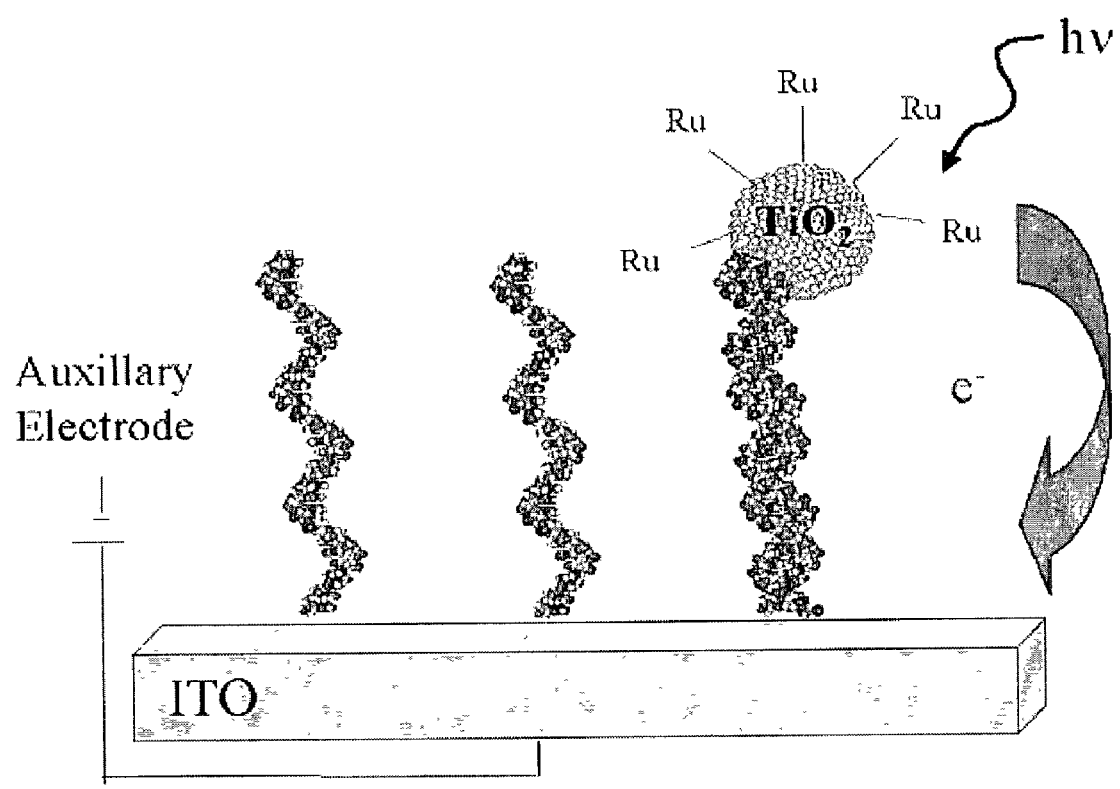
FIG. 1B is a diagram depicting an electrochemical detection strategy employing DNA-nanoparticle conjugates to carry redox molecules in accordance with the present invention.
Figure 2A:
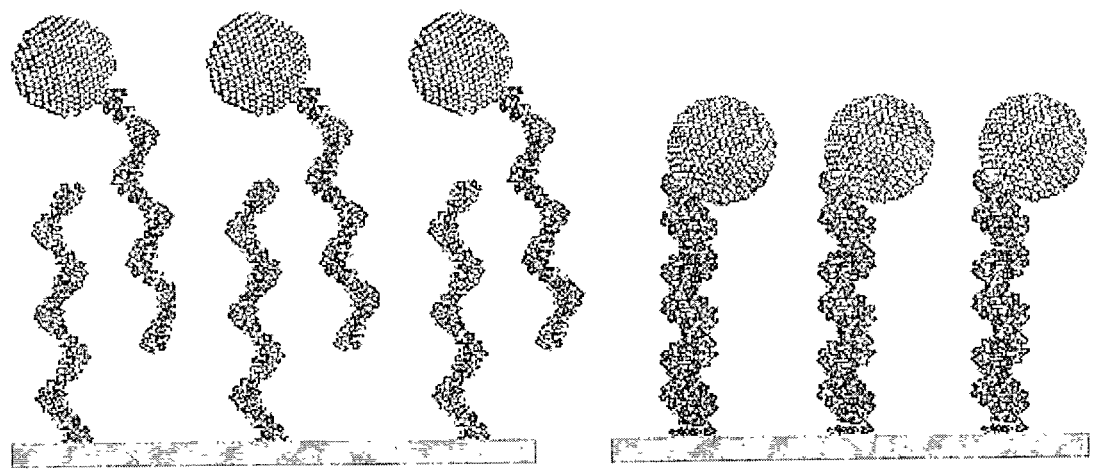
FIG. 2A is a diagram depicting an overall method of forming DNA duplexes that permit nanoparticle-based detection of the duplex. On the left side of FIG. 2A, nucleic acid sequences to be probed are bound to a support and presented to nanoparticle-containing nucleic acid probes. On the right side of FIG. 2A, nanoparticle-containing nucleic acid probes that are complementary in sequence to the support-bound nucleic acid sequences bind to the support-bound nucleic acid sequences.
Figure 2B:
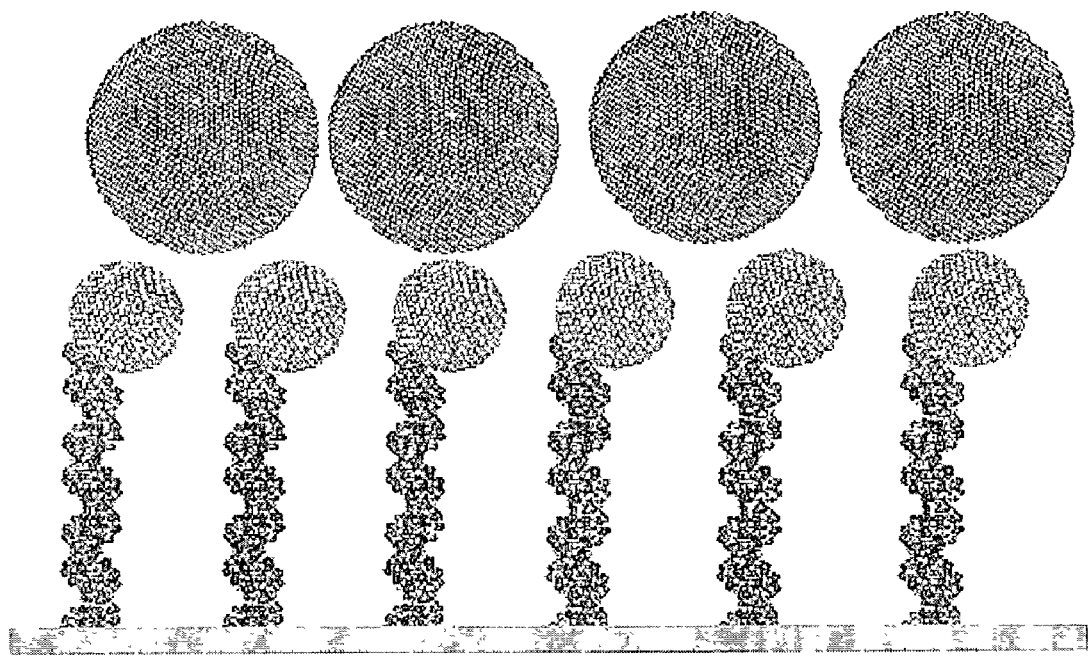
FIG. 2B is a diagram depicting DNA duplexes formed between support-bound nucleic acid sequences and nanoparticle-containing nucleic acid probes. An overlayer of particles that permits optical or electrochemical detection is also depicted.

A general scheme of one embodiment of the present invention is depicted in FIG. 2A. In FIG. 2A, target moieties (depicted as bent lines in the figure) are associated with 2 nm gold particles (depicted as spherical entities attached to the target moieties). In the lefthand side of FIG. 2A, surface-bound probe moieties are exposed to target moieties. Those probe and target moieties that associate with each other form duplexes, as shown in the righthand side of FIG. 2A. In FIG. 2B, formed duplexes are exposed to secondary entities, which can assist in detecting duplex formation. Some detection methods that can be employed in the present invention include electrochemical (i.e. detection of a photocurrent) and optical detection, which are illustrated schematically in FIGS. 1A and 1B, respectively.

To demonstrate one a method of the present invention, the embodiment of the present invention depicted in FIG. 1A was prepared. This figure depicts "charge hopping", a principle that forms an aspect of some methods of the present invention. In the "charge hopping" model, a charge generated on a nanoparticle is transferred (i.e. "hops") from the nanoparticle to a conductive support, thereby generating a detectable current in the support. In FIG. 1A, a charge (an electron) is depicted as being transferred from ferrocene to a gold support. This transfer generates a detectable current in the support. It is noted that ferrocene is included here as a secondary component to illustrate "charge hopping" in the context of an electrochemical embodiment of the present invention. Ferrocene was selected as an representative secondary component based on its redox properties.

In one electrochemical embodiment of the present invention, nanoparticles carry a target analyte and at least one, or optionally many, redox molecules (such as ferrocene) which are employed as a secondary component, as shown in FIG. 1A. The (target analyte-nanoparticle)-(surface-bound probe) binding event is detected by an electrode current through the support. The electrode serves as the support for the surface-bound probe.

In another embodiment of a photocurrent-based method of the present invention, nucleic acid-nanoparticle complexes and/or protein-nanoparticle complexes hybridize with probes (e.g. nucleic acids, small molecules, peptides) bound to the surface of a chip or other surface, and can be developed by dipping the chip into a solution comprising a photoelectrochemically active secondary component that associates with the primary nanoparticles. Light energy is then applied to the secondary component (for example, in the form of a laser beam) so as to liberate electrons, which will move toward the support. The presence of a photocurrent is detected by monitoring the current in the support. This scheme is depicted generally in FIG. 1B.

Secondary components can be, for example, larger particles or luminescent particles, which can allow detection using a number of different detection instruments, including fluorescence and UV spectrometers, microscopes and other instruments. Secondary components can also comprise photoelectrochemically active moieties, as depicted in FIG. 1B. Association of a photo-electrochemically active secondary component with a nucleic acid-nanoparticle complex or a protein-nanoparticle complex can be employed to facilitate various approaches for detection. When a photoelectric current is detected, a photoelectrochemically active secondary component can have the effect of amplifying the detected photocurrent, as well as facilitating the detection of a photoelectric current. The methods of the present invention described generally in FIGS. 1A and 1B are applicable for all types of nucleic acid-nucleic acid or protein-nucleic acid hybridization on a support or surface.

Alternatively, a photoelectrochemically active moiety can be an element of a target analyte-probe complex, such that a photoelectrochemically moiety is present in the hybridization complex. In this embodiment, the optional step of dipping the complexes into a solution comprising a secondary component is not required.

Electrochemical detection of a hybridization event at a surface is desirable due to the inherent sensitivity of the method. For example, coulometry can be used to measure the presence of femtomoles of material on the surface of an electrode. However, in array applications, there is an inherent limitation in the technique if addressable access to thousands of individual locations is required. By way of specific example, in a typical commercial "DNA chip", there can be up to 65,536 (i.e. $2^{16}$) different sequences chemically attached to a surface. If each of these sites is to be addressed by an individual electrode, very expensive miniaturized wiring is required to connect each of the 65,536 sites to a detection apparatus.

If instead the entire chip is placed on one electrode and the measurement of current is activated by a photoinduced electron transfer, as in one embodiment of the present invention, then the advantage of sensitive detection can be combined with the current size scale of microarrays. For example, photoinduced electron transfer can be measured by focusing a laser on one particular cell of the microarray (corresponding to a particular labeled probe that is attached at that point) and poising the potential of the electrode at a value where no current should flow in the dark, but where current will flow in the presence of light. Thus, the present invention discloses a method and system that can be employed in the detection of hybridization events occurring on a microarray. The present invention eliminates the need to individually wire each cell of the array to detect a hybridization event electrochemically by employing a single electrode.

Additionally, the present invention employs nanoparticles in the detection of hybridization duplexes. Metals, metal oxides, semiconductors, conductive polymers and any other conductive materials, for example, are materials that can be employed in the formation of nanoparticles. These materials can be selected based on their utility in the electrochemical detection of chemical phenomena and the ease with which nucleic acids can be bound to nanoparticles fashioned from these materials.

Thus, in one embodiment, a method of the present invention provides a nanoparticle comprising a target analyte and a photoelectrochemically active moiety. As discussed hereinabove, the providing of a nanoparticle comprising a target analyte and a photoelectrochemically active moiety can be accomplished in any suitable manner, as disclosed herein, including via the preparation of a nanoparticle. When a nanoparticle is prepared, a photoelectrochemically active moiety can form an element of a target analyte nanoparticle complex, or can be associated with a nanoparticle by contacting (e.g. by dipping) a substrate comprising the nanoparticle into a solution comprising a secondary component that associates with the primary nanoparticles, and additionally, is photoelectrochemically active.

III. Selection and Preparation of a Target-Nanoparticle Complex

In one embodiment, a nanoparticle complex of the present invention can comprise at least two components: a nanoparticle and a target analyte, such as a single stranded nucleic acid oligomer. In another embodiment, a target analyte can comprise a double stranded nucleic acid structure, and in yet another embodiment, a target analyte can comprise a peptide or a polypeptide. These two components can be prepared and joined together to contact a surface-bound sample (e.g. a single stranded nucleic acid sequence, a double stranded nucleic acid sequence, small molecule, a peptide or a polypeptide), while imparting the property of easy detection of a hybridization event.

III.A. Selection and Preparation of a Nanoparticle

A nanoparticle can comprise almost any material; however, metals, metal oxides, conductive polymers, dendrimers (e.g. branched dendrimers) and semiconductors are examples of some materials that can be employed. In one example, the nanoparticle can be polyvalent to accommodate a plurality of redox photoactive centers, and can hold and maintain multiple photoredox centers in sufficient proximity to the support (which functions as an electrode) to transfer charge to the electrode. Thus, a nanoparticle can be adapted to hold and/or maintain photoredox centers at a distance from the support to transfer charge to the support (i.e. electrode). A sensitizer or mediator can also be present that can facilitate carrying charge to the support, as in the charge hopping example discussed herein.

Some representative metals and metal oxides that can be employed in the present invention, for example as materials from which a nanoparticle can be formed, include titanium, titanium dioxide, tin, tin oxide, silicon, silicon dioxide, iron, iron$^{III}$ oxide, silver, gold, copper, nickel, aluminum, steel, indium, indium tin oxide, fluoride-doped tin, ruthenium oxide, germanium cadmium selenide, cadmium sulfide and titanium alloy. Gold and tin oxide ($TiO_2$) can also be selected, in view of their well-characterized reactivity and electrochemical profiles. Nanoparticles comprising the above materials and having diameters less than about 1,000 nanometers are available commercially or they can be produced using $HAuCl_4$ and a citrate-reducing agent or other reactants, using methods known in the art. See, e.g., Marinakos et al., (1999) *Adv. Mater.* 11:34; Marinakos et al., (1998) *Chem. Mater.* 10:1214-19; Enustun & Turkevich, (1963) *J. Am. Chem. Soc.* 85:3317. Various physical and chemical vapor deposition processes, such as sputter deposition, can be also employed. See, e.g., Hayashi, (1987) *J. Vac. Sci. Technol.* A5(4): 1375-84; Havashi, (1987) *Phys. Today*, December 1987, 44-60; *MRS Bulletin*, January 1990, pgs. 16-47. Tin oxide nanoparticles having a dispersed (in $H_2O$) aggregate particle size of about 140 nanometers are available commercially from Vacuum Metallurgical Co., Ltd. of Chiba, Japan. Other commercially available nanoparticles that might have a desired composition and size range are available, for example, from Vector Laboratories, Inc. of Burlingame, Calif.

Another consideration when selecting a material for a nanoparticle central component is the chemical reactivity profile of the material. The chemical reactivity profile of a material is a consideration, because other entities, such as oligonucleotides, will ultimately be associated with the nanoparticle central component. Additionally, it might be desirable to associate a secondary component (e.g. a photoelectrochemically active redox agent) with a nanoparticle central component. Therefore, the reactivity of a nanoparticle central component to a desired secondary component can also be a consideration. Thus, considerations when selecting and/or designing a nanoparticle central component can include size, material, chemical reactivity of the material the ease with which an oligonucleotides can associate with the nanoparticle central component, and the ease with which a secondary component can associate with the nanoparticle central component.

III.B. Selection and Preparation of a Target Analyte

In the present invention, single stranded nucleic acid oligomers, as well as double stranded nucleic acid oligomers, small molecules and proteins, can be employed as probes and target analytes. The reason for this choice is to facilitate the identification of a hybridization event, wherein a probe (e.g. a single stranded nucleic acid, a double stranded nucleic acid, small molecule, a peptide or a polypeptide) is bound to a surface and probed by a target-nanoparticle complex. In the following discussion, it will be appreciated that the terms "nucleic acid oligomer" and "nucleic acid sequence" encompass RNA (including mRNA), as well as DNA (including cDNA), and can comprise modified nucleic acid sequences, that is, sequences comprising modified nucleic acids.

In one embodiment, a single stranded nucleic acid oligomer selected for use as a target sequence in the present invention can be chosen on the basis of the context in which the present invention is employed. For example, a single stranded target sequence can correspond to a nucleic acid sequence known or suspected to be present in a disease condition. Functional equivalents of known sequences can also be used as target sequences and form an aspect of the present invention. Protein and nucleic acid sequences of any manageable length can be used as a target analyte. Typically, a nucleic acid target sequence is between 20 and 50 nucleotides in length, and thus target sequences of 25, 30, 35, 40 or 45 nucleotides can be employed. However, oligonucleotides of any length can be employed in the methods of the present invention. As noted herein, proteins and fragments of proteins of various lengths can also be employed as target sequences.

In another embodiment, a target analyte can also comprise a double stranded nucleic acid. Double stranded nucleic acid sequences can be prepared, for example, by isolating a double stranded segment of DNA. Alternatively, multiple copies of single stranded complementary oligonucleotides can be synthesized and annealed to one other under appropriate conditions.

When a target analyte comprises a nucleic acid sequence, the nucleic acid sequence can come from a variety of sources. For example, a nucleic acid that can serve as a target analyte can be isolated from a cell. Nucleic acids isolated from a cell can comprise, for example, intact or fragmented genomic DNA or mRNA. Alternatively, a nucleic acid can be derived from an isolated nucleic acid. For example, a target analyte can comprise a PCR product or an OLA product that have been synthesized using an isolated nucleic acid as a template. See, e.g., Nuovo et al., (1999) *J. Histol. Cytochem.* 47:273-279.

In yet another embodiment of the present invention, a target analyte can comprise an amino acid sequence, for example a sequence based on or derived from a protein. In this embodiment, a target analyte can be isolated from a biological sample or it can be prepared by enzymatically or chemically excising a selected sequence from the overall sequence of a protein. Alternatively, a target analyte can be synthesized from individual amino acids, either manually or via an automated protein synthesizer.

In the context of the present invention, all embodiments of a target analyte or a probe sequence can comprise a tag sequence. A tag sequence can comprise, for example, a sequence that is complementary to a support-bound tag complement. A tag sequence can be associated with a target analyte, which can then be amplified by PCR prior to association with a nanoparticle. The PCR amplicon will comprise a nucleic acid sequence comprising the tag sequence and a target analyte. The PCR amplicon then comprises a sequence that is complementary to a support-bound tag complement. Inclusion of a tag sequence, for example as a component of a target analyte, offers the advantage that a support need not be specific for a given target analyte, but rather can be universal in the sense that it is specific for a tag complement, but not for any particular target analyte. Thus, by employing a method comprising the use of a tag-tag complement approach, the need to form different supports for different probe and/or target analytes is mitigated. See, e.g., WO 94/21820, WO 97/31256, WO 96/41011 and U.S. Pat. No. 5,503,980.

When a target analyte comprises a nucleic acid oligomer, such nucleic acid oligomers can be prepared in a variety of ways, many of which will be apparent to those of ordinary skill in the art upon review of the disclosure of the present invention as set forth herein. For example, selected nucleic acids can be excised from a larger nucleic acid sample using restriction endonucleases, which sever nucleic acid sequences at known points in a nucleic acid sequence. Excised nucleic acid sequences can be isolated and purified by employing standard techniques. mRNA can also be isolated and purified by employing standard techniques. Target sequences can also be prepared by reverse transcription processes. See, e.g., Sambrook et al., (1992) *Molecular Cloning: A Laboratory Manual*, Cold Spring Harbor, N.Y. Alternatively, a nucleic acid sequence can be synthesized using well-known manual and automated nucleic acid synthesis methods. When nucleic acids are synthesized by an automated apparatus, a DNA synthesizer, such as the ABI™ 3900 High-Throughput DNA Synthesizer, available from Applied Biosystems, Inc. of Foster City, Calif., can be employed. Additionally, nucleic acids can be prepared by employing PCR to amplify a given nucleic acid sequence. In this method, isolated (or synthesized) single stranded nucleic acids can be employed as PCR templates. All nucleic acid oligomers to be used as probes, whether they are excised, synthesized or otherwise prepared, can be substantially pure.

III.C. Association of a Target Analyte with a Nanoparticle

After preparing a nanoparticle component and a target analyte (e.g., a single stranded or double stranded nucleic acid sequence, small molecule or a protein), the two components are joined as a complex. It is noted that different attachment chemistry can be employed, depending on the source of a target analyte. That is, some attachment methods are appropriate for attaching target analyte's that have been synthesized (a synthesized nucleic acid oligomer), while a different set of attachment methods are appropriate for attaching target analyte's that have been isolated or reverse transcribed (a non-synthetic nucleic acid oligomer). Yet other strategies can be employed when a target analyte comprises a double stranded nucleic acid sequence or a protein.

III.C.1. Attachment of a Synthesized Nucleic Acid Oligomer to a Nanoparticle

Figure 8:
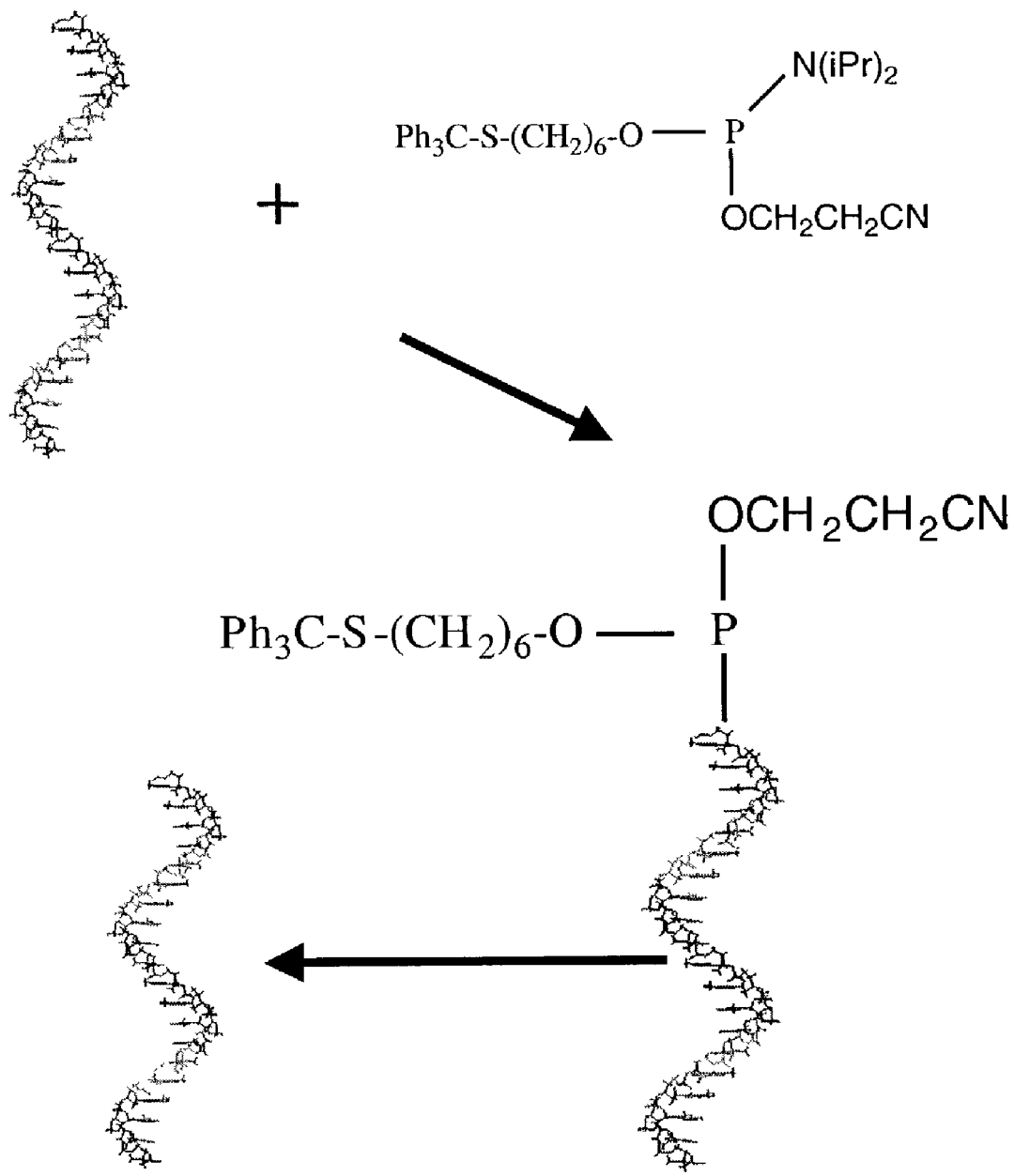
FIG. 8 is a schematic diagram depicting a method according to the present invention by which DNA molecules can be anchored to a nanoparticle.
Figure 9:
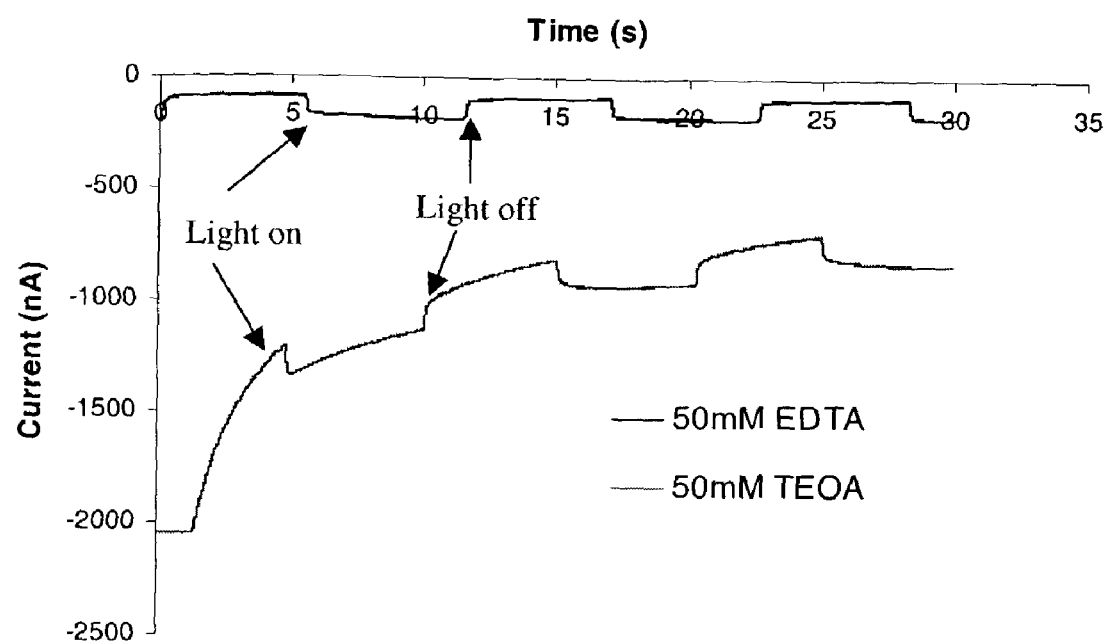
FIG. 9 is a plot depicting the dark current for TEOA and EDTA.

When attaching a synthesized nucleic acid to a nanoparticle central component, a thiolation reaction can be performed to add a thiol group to the 5' end of a single stranded nucleic acid oligomer. Alternatively, an amination reaction can be performed and will proceed *mutatis mutandis* with the thiolation reaction described herein. The general purpose of the reaction is to introduce a nucleophilic center that can subsequently be functionalized with a desired moiety, namely a nanoparticle of the present invention. As shown in FIG. 8 and immediately below, a suitable thiol modifier phosphoramidite reagent is the following compound, which is available from Glen Research, Corp. of Sterling, Va.:

Compound 1

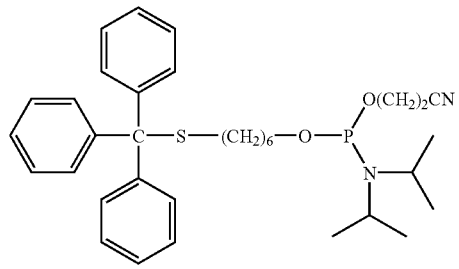

Continuing with FIG. 8, single stranded nucleic acid oligomers are incubated with a thiol modifier phosphoramidite under anhydrous conditions that permit attachment of the phosphine to the 5' end of the nucleic acid. The reaction can be carried out in a nucleic acid synthesizer under standard (and anhydrous) conditions. The thiol modifier is added in the last step of synthesis of an oligonucleotide. The phosphine is oxidized using iodine and the purification is exactly the same as that used for unlabeled oligonucleotides. The purification process is easier for labeled oligonucleotides since labeled oligonucleotides are significantly more hydrophobic and therefore tend to elute much more slowly under typical HPLC conditions. In this reaction, the thiol group is protected by a protecting trityl or acetic thioester group and is separated from the 5'-phosphodiester by a variable length carbon linker. A six-carbon linker is present in Compound 1.

The nucleic acid complex is then subjected to thiol deprotection to remove the trityl group. Specifically, the protecting trityl group is removed by treatment with silver nitrate and dithiothreitol (DTT). The nucleic acid complex is incubated with a nanoparticle central component. The two entities are joined at the thiol exposed by the removal of the trityl group during the deprotection reaction. The formed active agent-nanoparticle complexes (in this embodiment nucleic acid-nanoparticle complexes) can be maintained in the reaction vessel until use. This strategy can be employed in the attachment of a single stranded or double stranded synthesized nucleic acid probe to a nanoparticle.

III.C.2. Attachment of a Non-Synthetic Nucleic Acid Oligomer to a Nanoparticle

When a non-synthetic (i.e. isolated, extended or reverse transcribed) oligonucleotide is employed as a target analyte in the present invention, the oligo can be attached to the nanoparticle in a variety of ways. However, the attachment chemistry for non-synthetic oligos is different from that employed to attach a synthetic nucleic acid oligomer to a nanoparticle. Suitable attachment strategies are presented herein below.

One mechanism for attaching a non-synthetic oligonucleotide probe to a nanoparticle, generally described as an end-labeling scheme, involves derivatizing the 5' hydroxyl of an oligo to incorporate a functional group reactive with the nanoparticle material on the 5' end of the oligo. A representative, but non-limiting, list of functional groups includes a carboxylate group, an amine group and a thiol group. Such functional groups can be added to an oligo as a step in the synthesis of the oligo and can be programmed as an additional step in automated nucleic acid synthesizers.

In one embodiment of an attachment scheme, an oligonucleotide having a 5' hydroxyl group is incubated under suitable anhydrous reaction conditions with N,N' carbonyldiimidazole and subsequently with a cysteamine, thereby end labeling the oligo with a thiol group according to Reaction Scheme 1:

Reaction Scheme 1

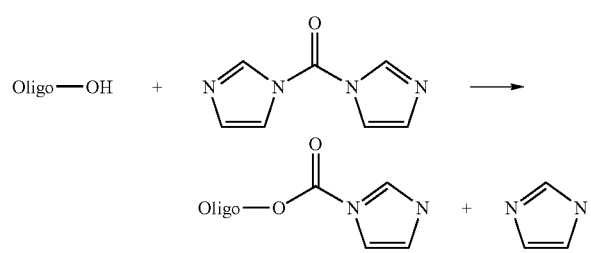

-continued

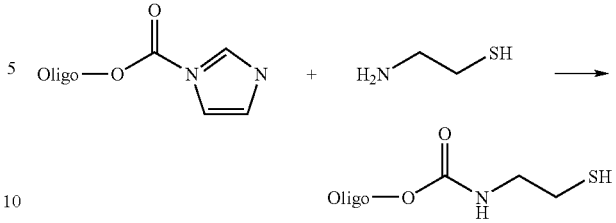

In yet another embodiment of an attachment scheme, a carboxylate (or a thiol, amine or any other moiety) moiety can be chemically incorporated into a reverse transcription reaction or, as noted, attached to the 5' hydroxyl of a synthesized oligonucleotide. Similarly, phosphonates and amines can be employed to attach an oligonucleotide to a metal oxide central component or a nanoparticle. Cystamine-based attachment strategies can also be employed. Those of ordinary skill in the art will recognize reaction conditions that might be damaging to an oligo (e.g. mRNA) and can design attachment strategies, using the above disclosure as a guide, so as to maintain the integrity of the oligo. It is noted that a deoxynucleotide phosphate (dNTP) having a 5' hydroxyl group can also be derivatized using Reaction Scheme 1 for attachment to a central component. Suitable protective groups and additional reaction conditions can be employed and will be known to those of skill in the art upon consideration of the present disclosure. The strategies discussed in this section can be employed in the attachment of a single stranded or double stranded non-synthetic nucleic acid to a nanoparticle.

III.C.3. Attachment of a Protein or a Small Molecule to a Nanoparticle

In one embodiment of the present invention, a protein or a small molecule can serve as a target analyte. The protein can be prepared as described herein and attached to a nanoparticle as follows. The small molecule can be synthesized according to known techniques, isolated from a sample, or even purchased from a commercial source.

Initially, it is noted that like methods of attaching a nucleic acid to a nanoparticle, thiol chemistry can be employed. For example, one representative method of attaching a protein or a small molecule to a nanoparticle comprises dissolving a thiol-containing coupling reagent, (e.g. N-succinimidyl-3-(2-pyridyldithio) propionate) in a solvent (e.g. 2,2,2-trifluoroethanol). A nanoparticle can then be suspended in the coupling reagent solution. The nanoparticle can then be removed, and transferred to a solution containing protein or small molecule material dissolved in a solvent (e.g. 2,2,2-trifluoroethanol). A volume of a second solvent (e.g. N,N-diisopropylethylamine) can then be added. After a desired period of time (e.g. 24 hours), the nanoparticle can be washed (e.g. with buffer) to remove any non-covalently bonded material.

Other methods of attaching a protein or a small molecule to a nanoparticle will be apparent to those of ordinary skill in the art upon consideration of the present disclosure.

IV. Selection, Preparation and Attachment of a Probe to a Support Surface

A probe of the present invention can comprise a single stranded nucleic acid sequence, a double stranded nucleic acid sequence or a protein, including sequences comprising non-standard nucleic acids and amino acids. Methods of preparing and attaching these probes to a support surface are discussed hereinbelow.

IV.A. Selection of a Probe

In one embodiment of the present invention, a single stranded nucleic acid sequence can be employed as a probe. For example, a single stranded nucleic acid sequence can comprise a cDNA sequence complimentary to a gene of interest. In another embodiment, a double stranded nucleic acid sequence can be employed as a probe sequence. A double stranded sequence that is employed as a probe sequence can comprise blunt ends (in which case there is no difference in the number of nucleic acids between the two strands), or sticky ends (in which case the there can be a difference in the number of nucleic acids between the two strands). In yet another example, a protein can serve as a probe sequence. A small molecule can also serve as a probe.

In these and other embodiments, a probe sequence can be selected as need or preference dictates. For example, a sample can comprise a nucleic acid sequence known or suspected to be associated with a genetic or physiological condition. In another example, a sequence suspected of harboring a mutation can be screened. In yet another example, a plurality of samples can be screened to confirm the absence of a given sequence or sequence mutation. In these and other embodiments, support surface bound nucleic acids can be samples isolated from a plurality of patients. The samples can be, for example, 20-50 nucleotides in length, although longer and shorter sequences can also be screened.

As noted herein, a tag sequence can be employed in the methods and compositions of the present invention. When a tag sequence is employed, a support can comprise a probe that comprises a tag complement. A tag complement is a sequence that is complementary to a sequence associated with a target analyte. Thus, when a target analyte comprising a tag sequence is contacted with a probe comprising a tag complement under suitable conditions, a duplex can form. Thus, when selecting a probe, in one embodiment, a probe can comprise a tag complement.

By employing a tag complement, a support can be independent of the source of a target analyte (e.g. species, etc.) in the sense that the support is specific for a tag complement, but not for any particular target analyte. Thus, by employing a method comprising the use of a tag-tag complement approach, the need to form different supports for different probe and/or target analytes is mitigated.

IV.B. Selection and Preparation of a Support

A suitable support can be selected based on any set of criteria. Supports useful for practicing the present invention can be constructed from any conductive material to which a thio-alcohol linker or other linker, and consequently its associated target sequence, can bind. In some embodiments, gold and/or indium tin oxide can be employed as supports. Alternatively, a support can be constructed from a nonconductive material, such as the high density polyethylene (HDPE) used in 96-well titer plates, that has been coated with a conductive material. In yet another example, a polyacrylamide gel can be employed (Dubilev et al., (1997) *Nucleic Acids Res.* 25: 2259-2265). A support that is conductive can be employed in the electrochemical detection of a hybridization event.

An additional criterion to consider in selecting a support suitable for use in the present invention is the location addressability of the support. That is, a support can be constructed so as to permit a plurality of probes (e.g. single stranded nucleic acids, double stranded nucleic acids, small molecules or proteins) to be attached to the support in identifiable locations. Such a structure is generally referred to as an array. This arrangement facilitates the screening of a plurality of unique samples. It is, of course, desirable to know the identity of each sample, so as to be able to correlate positive and negative binding events. This can be accomplished by maintaining records of the identity of the sample bound at a discrete point on the surface.

IV.C. Preparation and Attachment of a Probe to a Support Surface

The identity of a probe bound to the support at a given location can be determined in different ways. As noted above, one way to correlate a probe with its location is to attach the probe to the support at a known position (see, e.g., Pirrung, (1997) *Chem. Rev.* 97: 473-486). Discrete locations on a support can be identified using a grid coordinate-like system. In this approach, the working area of the support surface can be divided into discrete cells. Different probes can subsequently be attached to the surface in an orderly fashion, for example, one probe nucleic acid oligomer per cell. In this strategy, the probe oligomers can be applied one or several at a time. In one exemplary method, sites at which it might be desirable to temporarily block probe binding can be blocked with a blocking agent. The blocking agent can be subsequently removed and the site freed for probe binding. This process can be repeated any number of times, thus facilitating the attachment of a known probe at a known location on a support.

Another strategy for localizing probes to a support surface at known locations involves the use of microspotting. In this approach, the location of the probes on support surface is determined by the ordered application of samples in a group. That is, probes are ordered in known locations prior to application to the support surface. In this way, the location of each probe is known as it is applied, and differs from the previous approach, which requires that each sample be applied to a known location on the support surface. Appropriate devices for carrying out this approach are commercially available and can be used in the context of the present invention. For example, the present invention is compatible with the commercially available GENECHIP™ system (Affymetrix, Inc., Santa Clara, Calif.).

In one embodiment, a probe can be prepared for and anchored to a support surface using the following representative method. Initially, a probe is synthesized or isolated from cells or other source. There is no requirement that the cells be derived from mammalian (e.g., human) or vertebrate sources. In fact, the present invention can be used to screen probe sequences derived from bacterial cells, yeast and other fungal cells or from other microorganisms. Samples derived from invertebrate sources (e.g., insects, nematodes or other commercially relevant invertebrates) can also be screened. Samples obtained from plants can also be screened.

Large molecules comprising one or more probes (e.g. genes and long sequences of single stranded nucleic acids, double stranded nucleic acids and proteins) can be enzymatically or chemically severed into smaller more manageable oligomers. If desired, double stranded nucleic acid samples are denatured (e.g., by heating to melt hydrogen bonds) to generate single stranded nucleic acid sequences. Care should be taken to assure that palindromic sequences present on the same nucleic acid sequence do not self-anneal, which could prevent recognition and hybridization with a complementary probe. Such difficulties can be avoided by strategic cleavage of larger nucleic acid sequences. Standard methods for nucleic acid isolation, purification and cleavage (see, e.g., Sambrook et al., (1992) *Molecular Cloning: A Laboratory Manual*, Cold Spring Harbor, N.Y.) and protein purification and cleavage (see, e.g., Janson & Ryden (eds), (1998) *Protein Purification: Principles, High Resolution Methods, and Applications*, 2nd ed., Wiley-Liss, New York) are known in the art.

Following the preparation of one or more probes, the probes can be attached to the surface of a support using any suitable attachment approach, such as those disclosed herein and those that would be apparent to one or ordinary skill in the art after review of the present disclosure. When a probe sequence comprises a single or double stranded nucleic acid sequence, these sequences can be, for example, substantially pure nucleic acid sequences of a desired length and composition, and can be homogeneous or heterogeneous with respect to sequence.

In one example of an attachment approach suitable for attachment of nucleic acid sequences to a support, one or more probe sequences are initially incubated with a solution of a thio-alcohol for a preselected period of time. In one embodiment of the present invention, C6 mercaptohexanol can be employed as a thio-alcohol. Thio-alcohol and nucleic acid are added in amounts so as to bring the final concentration of nucleic acid in the solution to about 20% or less. The incubation time permits the covalent association of the 3' end of the nucleic acid oligomer with the hydroxyl group of the thio-alcohol. The solution is then exposed to the surface of a support under conditions that permit association of the sulfur atom of the thio group with the surface of the support. The benefits of this process are twofold: it serves not only to attach a probe nucleic acid to the support surface but additionally adds a linker group, which corresponds in distance to the length of the alkyl group separating the thio and alcohol groups of the thio-alcohol, in order to distance the nucleic acid oligomer from the surface. Suitable equipment is commercially available and can be used to assist in the binding of a target sequence to a support surface.

IV.D. Passivation of a Support Surface

Following attachment of a probe to the surface of the support, the points of the surface to which no probe is bound can be passivated. As used herein, the term "passivation" generally means the alteration of a reactive surface to a less reactive state. Passivation can refer to, for example, decreasing the chemical reactivity of a surface or to decreasing the affinity of a surface for protein, small molecule or nucleic acid. Stated differently, passivation is a method by which a surface is coated with a moiety having the ability to block subsequent binding to the surface at points where the moiety is bound. A passivation process can be implemented after probes are bound to the support, and can include sequential synthesis and co-deposition approaches, as disclosed herein.

In one embodiment, passivation is accomplished by exposing the surface to thio-alcohol, as described above. For example, the same thio-alcohol can be used to passivate the surface as was used in attaching the probe to the surface. In other embodiments, thio-alcohols of shorter or longer length can be employed.

In another embodiment, other molecules, i.e. "passivation moieties" can be used passivate the surface of a support. For example, polyethylene glycol (PEG), various alcohols (as noted above) and carboxylates can all be used to passivate the surface of a support, as can COO— and $CONH_2$ moieties. In some embodiments, passivation moieties can also be non-covalently or covalently attached. For example, passivation can include covalent attachment of silyl chloride, thiol, gold, silver, a sol gel, and the like, to a metal or metal oxide support. Indeed, virtually any material can be used to passivate a support surface, with the caveats that the material must associate with the support to form a protective layer coating the support, and that the passivating process, which can be performed after a probe is already associated with the surface of the support, does not damage any probes already bound to the support.

A passivation step can be performed to reduce the potential for nonspecific association between a nanoparticle complex and a support. Following the passivation of the support, a mixed monolayer is created on the surface of the support. The mixed monolayer can comprise one or more copies of a probe bound to the surface and a passivating material. The term "mixed monolayer" then generally refers to the passivated surface of a support to which a probe has been bound.

V. Duplex Formation

After a probe or target analyte has been attached to a support surface and target analyte-nanoparticle complexes or probe-nanoparticle complexes have been prepared (and optionally after the surface has been passivated), a hybridization reaction is performed. Generally, a support-bound probe is exposed to the target analyte-nanoparticle complexes. Alternatively, a support-bound target can be exposed to a probe-nanoparticle complex. If the probe and target analytes have an affinity for one another, the target analyte-nanoparticle (or probe-nanoparticle), will form a duplex with the support-bound moiety, to thereby provide a support comprising a target or a probe attached thereto.

Thus, as noted above, the probe and/or the target analyte can comprise an unknown, and either can be provided on the support. Generally, for convenience and in accordance with what is believed to be an art-recognized nomenclature scheme, the term "probe" is used here in when referring to a support-bound moiety.

For example, a probe can comprise a single stranded nucleic acid sequence and a target analyte can also comprise a single stranded nucleic acid sequence. If the two sequences are complementary to one another (using standard Watson-Crick base pairing rules), a double stranded hybridization duplex is formed between the two nucleic acid strands.

In another example, a probe (or a target analyte) can comprise a single stranded nucleic acids and a target analyte (or a probe) can comprise a multiply stranded nucleic acid structre (e.g. a double stranded nucleic acid sequence). If the probe and target analyte have affinity for one another, a multiply stranded hybridization duplex (e.g. a triple stranded structure or triplex) is formed between the sequences.

In yet another example, a probe can comprise a protein and a target analyte can comprise a protein. If the probe and target analyte have affinity for one another, a protein-protein hybridization duplex is formed between the sequences.

In a further example, a probe (or a target analyte) can comprise a nucleic acid sequence and a target analyte (or a probe) can comprise a protein sequence. If the probe and target analyte have affinity for one another, a nucleic acid-protein hybridization duplex is formed between the sequences.

In an additional example, a probe (or a target analyte) can comprise a small molecule and a target analyte (or a probe) can comprise an moiety known or suspect to associate with the small molecule. More specifically, a probe-target pair can comprise a small molecule and a receptor. If the receptor and small molecule have affinity for one another, a small molecule-receptor hybridization duplex can form. Receptors can be proteins.

In another example, a probe (or a target analyte) can comprise an antibody and a target sequence (or a probe) can comprise an antigen, which can comprise any chemical moiety (e.g. a peptide, protein, small molecule, nucleic acid, etc.). If the antibody and the antigen have affinity for one another, an antibody-antigen duplex can form.

It can be desirable to maintain reaction conditions conducive to the formation of duplexes. For example, when nucleic acids are employed as probe and/or target sequences, high stringency conditions can be employed so as to minimize nonspecific duplex formation. Similarly, when probe and target sequences comprise protein sequences, conditions conducive to the formation of protein-protein interactions (e.g. pH, the presence and nature of any solvents or buffers present and the presence and nature of any ions present) can be maintained. Generally, hybridization conditions can be altered to fit the stringency requirements of an experiment or operation.

V.A. Treatment of Formed Duplexes with a Ruthenium-Based Secondary Component

After exposing a target analyte to a support and allowing hybridization duplexes to form and thereby provide a support having a target analyte attached thereto, the support can be further treated with a secondary component. For example, in an embodiment of the present invention that encompasses photoelectric detection of formed duplexes, the support and the associated duplexes can be treated with a secondary component characterized by an ability to associate with a central component of the nanoparticle, i.e. a photoelectrochemically active secondary component. In this embodiment of the present invention, compounds comprising ruthenium can be employed as secondary components. For example, $Ru(bipy)_3^{2+}$ can be employed as a ruthenium-based secondary compound.

In the photoelectric detection embodiment of the present invention, the secondary component, e.g., a ruthenium-based compound, associates only with central components, and therefore will not bind to surface-bound samples that have not formed duplexes. Any duplexes formed comprise the central component of a nanoparticle and thus can serve as a substrate for secondary component (e.g., ruthenium) binding.

Continuing with a photoelectric detection embodiment of the present invention, an association between the central component of a formed duplex and the secondary component (ruthenium or other photoinduced electron donor-based compound) can be formed by contacting the substrate containing the duplexes with a solution of the selected secondary component. For example, the substrate can be dipped into a solution containing one or more compounds; for example, compounds comprising ruthenium.

V.B. Treatment of Formed Duplexes with Other Secondary Components

Treatment of formed duplexes with a secondary component other than a ruthenium-based secondary component forms an aspect of the present invention. The nature of a secondary component and can be dictated by the desires of a researcher and the requirements of an experiment. Some secondary components can facilitate the use of different detection methods. For example, a fluorescent moiety that will associate with the metal atoms of a nanoparticle, while not associating with unbound probe, can facilitate fluorescent detection of formed duplexes. Other spectroscopically active moieties can facilitate detection of formed duplexes using UV, visible or IR spectroscopy. Such moieties will be evident to one of skill in the art after reviewing the present invention as disclosed herein.

Protein-based secondary components can also assist in duplex detection. For example, an ELISA-like duplex detection system might be suitable in a given situation. Alternatively, a detectable protein or small molecule can be employed as a secondary component. As noted herein, due to the physical size of the nanoparticles involved STM does not require a secondary component, although a suitable secondary component can be employed as circumstances dictate. Additional details of duplex detection and the role of some secondary components are discussed below.

VI. Detection of Duplexes

The present invention facilitates detection of formed nucleic acid duplexes by a variety of methods including STM, fluorescence and electrochemical techniques, but most notably by detection of a photocurrent. Various methods of detecting duplex formation are described more completely herein below.

VI.A. Scanning Tunneling Microscopy

Scanning tunneling microscopy (STM) can be used to generate images of formed duplexes. For example, nucleic acid duplexes comprising nanoparticles of 5 nm and larger can be clearly visualized by STM, as evidenced by the STM images presented in FIGS. 3 and 5. FIG. 3 depicts nucleic acid duplexes comprising 5 nm nanoparticles, while FIG. 5 depicts nucleic acid duplexes comprising 10 nm nanoparticles. In both figures, DNA was used as both the probe and the target sequence.

FIG. 3 indicates that 5 nm nanoparticles form sparse monolayers below a concentration of DNA below 10%. These sparse monolayers can also be detected by STM. When employing STM, one consideration is the presence of duplexes, which can be more significant than the limitations of the STM detection technique. Thus, STM can be used to detect the presence of hybridization events. On one embodiment, when STM is employed to detect duplex formation, the position and identity of the probe are known. In other embodiments, the position and/or the identity of the probe can vary.

STM can also be used to estimate the density of nanoparticles on a surface and, consequently, the number of duplexes formed. A density calculation can be performed by counting the number of observed particles in a given area scanned by STM. An understanding of the density of duplexes on a surface can provide information regarding the sequence requirements for a given probe. As described herein, the present invention can be useful in probe design and can give an indication of the tolerance requirement for a potential probe to function in a desired manner.

Another advantage of employing STM to detect duplex formation is that STM can give accurate measurements perpendicular to the plane of the surface when operated in height mode.

VI.B. Electrochemical Detection of Duplexes

As depicted schematically in FIG. 1A, electrochemical detection strategies can be employed to detect duplex formation (e.g. nucleic acid sequence-nucleic acid sequence, nucleic acid sequence-protein, protein-small molecule, or protein-protein) in the present invention. In one embodiment of the present invention, a probe nucleic acid sequence is bound to a support comprising a conductive material, such as gold. Continuing with this embodiment, the support-bound probe nucleic acid sequence is exposed to a nanoparticle comprising a target nucleic acid sequence associated with a central component. Complementary nucleic acid sequences hybridize to form duplexes that comprise the nanoparticle central component (which remains associated with the target sequence upon hybridization).

Optionally, the support and any bound duplexes can subsequently be exposed to a secondary component, which comprises a redox compound. For example, ferrocene (i.e. discyclopentadienyl iron) can be employed as a redox compound. Ferrocene molecules are small, relative to the size of a nanoparticle of the present invention. Ferrocene can be labeled with an alkane thiol. A general strategy for attachment of a molecule to a gold nanoparticle (or a CdS, a CdSe or a silver nanoparticle) can include the use of thiols. Other possible molecules that can be used in an attachment process include isocyanate groups, phosphines and amines, although the latter can exhibit weaker interactions.

After forming duplexes on a support, or after treating the support with a secondary component, a current is applied to the support, which, due to its composition, acts as an electrode. When an electrical current is applied to the support, current travels through the support and interacts with the central component of a bound nanoparticle to generate a signal. The signal is amplified by the presence of the many redox active or photoredox active particles (i.e. a secondary component) associated with a nanoparticle. The current flows back to the electrode, completing a circuit and generating a detectable signal.

A nanoparticle itself can serve as a "redox-active signal". That is, a single gold nanoparticle comprises tens of thousands of gold atoms that can be oxidized to $Au^{3+}$ ions. This oxidation reaction can be detected electrochemically. This approach offers the advantage that the amplification factor is very large.

One advantage of this detection technique is that the current is proportional to the light flux on the sample. Like fluorescence detection methods, this is an extremely sensitive method and can be limited mainly by decomposition of the compounds on the surface.

VI.C. Fluorescent Detection

Targets and/or probes can be detected using the present invention by employing a fluorescence-based detection method. In one embodiment of a fluorescence-based detection method of the present invention, a probe nucleic acid sequence is bound to a support comprising a conductive material, such as gold. Continuing with this embodiment, a support-bound probe nucleic acid sequence is exposed to a nanoparticle comprising a nucleic acid target sequence and a central component. Complementary nucleic acid sequences hybridize to form duplexes that comprise a central component (which remains associated with the target sequence upon hybridization). Thereafter, the support, and any targets and/or probes bound thereon are exposed to a secondary component, which comprises a fluorescent compound. A variety of fluorescent compounds are available (e.g. Oregon Green and Texas Red) and will be known to those of ordinary skill in the art, upon consideration of the present disclosure.

After treating the support with a suitable fluorescent secondary component, fluorescence is detected using a fluorimeter or other instrument. Since the fluorescent secondary components will only associate with a nanoparticle central component, fluorescence will only appear at those locations of an attachment on the support. Fluorescence-based methods are very sensitive in general and thus, a fluorescence-based detection scheme can be advantageously employed to detect the presence of low concentrations of targets and/or probes (e.g. duplexes).

VI.D. Photocurrent Detection

A photocurrent detection method of the present invention offers significant advantages over detection systems known in the art. One particular advantage is the elimination of any requirement for individually wired sample cells. Commercially available microarray supports suitable for electrochemical detection of nucleic acid duplexes require that each sample be attached to the support at a different electrode. That is, duplex formation at each attachment point must be monitored by detecting a current through an electrode dedicated to each individual cell. The present invention can employ only a single electrode and achieves detection at each target analyte attachment point on the electrode by detecting current flow following irradiation of each target analyte attachment point by a light source, for example a laser beam.

In one embodiment of the photocurrent method, probes are bound to a conductive support. In one embodiment, a conductive support material comprises indium tin oxide. The support can be constructed entirely of a single conductive material or the conductive material can be layered over a second material, such as a multiwelled (e.g. 96-, 384-, or 1536-well) plastic plate. In some applications, it can be desirable to place target analytes at known positions on the support. In other applications it is not necessary to know which probes are located at which position on a plate. Commercially available microspotting equipment, such as the SPOTBOT™ Automated Spotting Arrayer (TeleChem International, Sunnyvale, Calif.), can be used to assist in sample placement. The support can also be wired with an auxiliary electrode depending on the detection configuration desired.

Nanoparticles comprising target analytes (or probes) can be prepared and a hybridization reaction performed, as described herein to provide a support having a target analyte attached thereto. Briefly, a target analyte is bound to a nanoparticle component, which can comprise a material such as metal, metal oxide, semiconductor, polymer or other material. Optionally, nanoparticles can be coated on their surfaces with electroactive molecules. The target analyte-nanoparticle complex is subsequently contacted with the support. When probe and/or target sequences comprise nucleic acid sequences, high stringency hybridization conditions can be employed, although the conditions can be varied with the needs of the experiment.

Following hybridization and attachment, the support can be treated with a secondary component. In one embodiment of a photocurrent method of the present invention, the secondary component can comprise a photoelectrochemically active compound. The presence of a photoelectrochemically active secondary component can be advantageously employed to enhance detection by boosting an observed photocurrent. More specifically, when a photoelectrochemically active secondary component is employed, a photocurrent arising from the central component and a photocurrent arising from the secondary component can interact to provide an additive effect. In one embodiment, a secondary component comprises a ruthenium center, such as ruthenium bipyridine, $Ru(bipy)_3^{2+}$. In some embodiments, primary nanoparticles can comprise titanium dioxide ($TiO_2$), gold, semiconductors, polymers or other conductive materials. Again, the size of a secondary component, as compared with the size of the nanoparticle component, is small, providing a plurality of secondary components to be localized to a single attachment point.

Continuing with the photocurrent detection method, detection can be achieved by irradiating the samples individually with a light source. The potential of the support electrode is poised so that current will flow only when light impinges on a nanoparticle carrying redox centers. The light source can be, for example, a laser having a wavelength that will vary with the chemical composition of the secondary component. In one specific example, when $Ru(bipy)_3^{2+}$ is employed as a secondary component, the wavelength of a laser can be 450-600 nm.

In some embodiments, a light source can be configured so as to allow irradiation of samples individually and sequentially, for example when a plurality of samples is being scanned. When a laser is used, the beam can be rastered across the support in a predictable pattern, such as horizontally or vertically. The rastering motion can be staggered so as to permit irradiation and detection of a current carried by a given sample (e.g. a that probe that formed a nanoparticle-comprising duplex), before a subsequent (e.g. sequential) sample is irradiated and monitored for the presence of a current.

Irradiation of a photoelectrochemically active secondary component causes electrons to travel to the support electrode. When photocurrent detection is employed, targets and/or probes (which can, for example, be present in duplexes) can be identified by monitoring photocurrent induced by light incident on photoelectrochemically active moieties associated with electrode, such as a support. The incident light interacts with the photoelectrochemically active moiety, which liberates electrons (i.e. a charge) from the photoelectrochemically active moiety. The charge then "hops" from the vicinity of the photoelectrochemically active moiety to the support, which is monitored for a change in current. This phenomenon is known as "charge hopping" and is described herein. The flow of a charge from the photoelectrochemically active moiety to the support generates a detectable photocurrent. The current in the support, which comprises a conductive material, is monitored for changes in current due charge hopping from a photoelectrochemically active moiety, associated with the target and/or probe, to the support. A positive current flow is indicative of attachment (e.g. duplex formation). The photocurrent detection method employed in the present invention is a light-dependent method. Therefore, a support can be rapidly scanned by a location-addressable light source, such as a xenon arc lamp or a rastering laser beam.

An advantage of the photocurrent method is the ability to wire a single electrode, for example a support structure, for detection, rather than wiring an individual electrode for each sample. This eliminates the need for cumbersome equipment, tedious sample preparation and attachment, and time-consuming, cost-prohibitive microelectronic operations.

VII. Applications of the Present Invention

The present invention can be employed to monitor hybridization events in a variety of different systems and models. As described more fully below, the present invention is particularly useful in the monitoring of gene expression, the detection of spontaneous or engineered mutations, in the design of probes, and in the identification of non-nucleic acid interactions. Generally, in applications wherein nucleic acid sequences are being selected and manipulated, care should be taken wherever possible to minimize the potential for the formation of self-annealed structures. For example, sequences that are predicted to give rise to self-annealing structures can be deliberately avoided when practicing the compositions and methods of the present invention.

Additionally, when a nucleic acid sequence is employed as a probe and/or target sequence, the stringency of hybridization conditions can be varied, with the general rule that the temperature remain within approximately 10° C. of the duplex's predicted $T_m$, which is the temperature (under defined ionic strength and pH) at which 50% of the target sequence hybridizes to a perfectly matched probe. An example of stringent hybridization conditions for analysis of complementary nucleic acids having more than about 100 complementary residues is overnight incubation in 50% formamide with 1 mg of heparin at 42° C. A high stringency wash can be preceded by a low stringency wash to remove background probe signal. An example of medium stringency wash conditions for a duplex of more than about 100 nucleotides is incubation for 15 minutes in 1×SSC at 45° C. An example of low stringency wash for a duplex of more than about 100 nucleotides is incubation for 15 minutes in 4-6× SSC at 40° C. For short sequences (e.g., about 10 to 50 nucleotides), stringent conditions typically involve incubation in salt concentrations of less than about 1.0 M sodium ion, typically about 0.01 to 1.0 M sodium ion (or other ion) concentration, at pH 7.0-8.3, at a temperature of at least about 30° C. Stringent conditions can also be achieved with the addition of destabilizing agents such as formamide. In general, a signal to noise ratio of 2-fold (or higher) than that observed for an unrelated probe in the particular hybridization assay indicates detection of a specific hybridization.

VII.A. Gene Expression Analysis

The present invention can be used to monitor gene expression in a model system. Although gene expression analysis using microarrays is known (Duggan et al., (1999) *Nature Genet. Supplement* 21: 10-14; Bowtell, (1999) *Nature Genet. Supplement* 21: 25-32), unlike the present invention, currently available methods employ optical-based approaches (e.g. fluorescence), which suffer from the drawbacks discussed above.

It is fundamental that the expression of a gene of interest correlates with the production of mRNA transcribed from the gene's DNA sequence. Transcribed mRNA is subject to standard Watson-Crick base pairing rules. Thus, a hybridization event involving a single stranded DNA oligomer corresponding to a gene of interest and a complementary mRNA sequence is indicative of the expression of the gene. In one embodiment, gene expression can be monitored as follows.

First, single stranded DNA derived from a gene of interest (i.e. a probe sequence) is attached to a suitable support. Unexpressed sequences of DNA, for example introns, can be removed before the samples are attached to the support. In this application, it can be desirable to employ cDNA as a probe sequence. Control samples of unrelated single stranded DNA can also be included and serve as an internal validation of the experiment.

Total mRNA is then isolated from an expression system using standard techniques. mRNA can be fragmented for ease of handling. mRNA is then attached to the central component of a nanoparticle as described hereinabove. The nucleic acid-nanoparticle complex is then contacted with the support-bound target single stranded DNA. In one embodiment of the method, conditions of high stringency are maintained, although these conditions can be varied with the needs and goals of the experiment. The support is washed to remove any unhybridized sample and then exposed to a secondary photoelectrochemically active nanoparticle. A method of exposing the support to a secondary component is simply by dipping the support in a solution comprising the secondary component. Again, a central component of a nucleic acid-nanoparticle complex can comprise $TiO_2$, and a compound comprising a ruthenium center can be employed as a secondary component.

The support is then irradiated by a light source, such as a laser. Electrons transferred by the secondary component are detectable by monitoring current flow in the support, which comprises a conductive material such as ITO, and thus serves as an electrode. Gene expression can be determined by comparing duplex formation by the control sequences to duplex formation observed in the target samples. Appropriate mathematical descriptions and treatments of the observed duplex formation can indicate the degree of observed hybridization and consequently the degree of gene expression.

VII.B. Mutation Detection

In another embodiment, the present invention can also be employed in the detection of mutations in a nucleic acid sequence. Although mutation analysis using microarrays is known (Hacia, (1999) *Nature Genet. Supplement* 21:42-47), unlike the present invention, currently available methods employ optical-based approaches (e.g. fluorescence), which suffer from the drawbacks discussed above. Such mutations can engineered or spontaneous. For example, the present invention can be useful in determining whether an engineered mutation is present in a nucleic acid sequence, or for determining if a nucleic acid sequence contains deviations from its wild type sequence.

In this embodiment, single stranded probe nucleic acid samples are initially prepared. The probe sample can be known or suspected to contain a mutation(s) to be identified. These probe samples are attached to the support using methods described hereinabove. Nucleic acid target sequences to be screened for the mutation are isolated from an expression system, and single stranded sequences are prepared. Large quantities of sample can be conveniently prepared using established PCR methods. Target sequences are bound to a nanoparticle, and the complex is contacted with the support bound probe sequences. Those probe sequences containing the mutation of interest will hybridize with the target sequence to form detectable duplexes. Unbound target sequences are removed by washing. The support, which can comprise any formed duplexes, is then optimally exposed to a secondary component, for example a photoelectrochemically active or electroactive nanoparticle. It is noted that in this embodiment, a mutation can be located on either a target analyte or on a probe sequence, the selection of which can be made during experimental design.

Duplexes can be detected as described herein above. In one example, a light source, such as a rastering laser beam, can be used to irradiate discrete points on the support, correlating to the placement locations of the probes on the support. When a photoelectrochemically active secondary component is employed, duplexes can comprise a photoelectrochemically active compound and irradiation generates a current that is detected by monitoring the current through the support electrode. Each probe (and therefore each potential site of duplex formation) is irradiated, and any generated current detected, in a sequential fashion, as can be accomplished through the use of a rastering light source.

VII.C. Probe Design

In yet another embodiment, the present invention can be employed in designing nucleic acid probes. The ability to detect hybridization events permits a researcher to optimize a probe for the needs of a given experiment. For example, a probe can be designed that will accommodate a degree of polymorphism in a target sample. Such a probe can be useful for screening for genes or sequences known to exhibit polymorphisms. Using the present invention, it is possible to design a probe that will tolerate a degree of uncomplementarity in the sequence.

Additionally, the present invention can be useful as a method of screening for duplex formation between a sequence and a polymorphic probe; that is, a probe that has one or more mutations from the wild type sequence. By varying the number of bases different from the wild type sequence, a desired degree of promiscuity in a probe can be obtained.

In this context, the present invention can be useful for detecting hybrid formation in sequential rounds of probe design. For example, if a designed probe binds only to the wild type sequence, no polymorphism is recognized; if the probe binds to sequences unrelated to the target sequence, the probe is not useful to identify the sequence of interest. By monitoring hybrid formation at each round of optimization, the present invention can be useful for nucleic acid probe design.

VII.D. Identifying Molecular Interactions

Although the discussion to this point has been focused on the use of the present invention as a method of monitoring hybridization between nucleic acid sequences, the present invention is also useful for monitoring the formation of protein-protein, peptide-peptide, protein-peptide, and protein-small molecule (e.g. receptor-ligand) complexes, as well as antigen-antibody complexes and protein-nucleic acid complexes.

Procedurally, the formation and detection of such complexes generally parallels the disclosed formation of nucleic acid duplexes. In one embodiment, a collection of probe proteins are attached to a support electrode, via chemical bonds. A target protein-nanoparticle complex is prepared, wherein the protein is known or suspected to interact with one or more of the probe proteins. The target proteins are exposed to the probe protein and allowed to interact. Excess target is removed in such a way as to preserve any protein-protein interaction. Optionally, the support and its formed associations can then be contacted with a secondary component. When a photoelectrochemically active secondary component is selected, the presence of associations between proteins can be detected by exposing the support to a light source (for example by rastering a light source over the support) and detecting any generated current.

VII.E. Identifying Single Base Mismatches

One of the major challenges of DNA microarray technology is the differentiation of two strands of DNA that are fully complementary and two strands of DNA comprising a single base mismatch. The use of applied electric fields to discriminate between a single base mismatch and complete complementarity has been demonstrated (e.g., the NANOCHIP™ from Nanogen, Inc. of San Diego, Calif.). However, the electric field required to identify a single base mismatch is fairly high, since the charge density on a single strand of DNA is relatively low. For example, a 25 mer single-stranded DNA (length ~8.2 nm, diameter ~1.5 nm) can have a charge density of ~2 $C/nm^3$.

If the single-stranded DNA is attached to a nanoparticle loaded with negatively charged ligands (e.g., bis(p-sulfonatophenyl)phenylphosphine), (BSPP) then the overall charge density of the ssDNA-nanoparticle complex that needs to be removed is dramatically increased. Assuming that ~1000 molecules are on the surface of the nanoparticle, then the overall charge density of a 5 nm nanoparticle is ~10 $C/nm^3$ by itself. This indicates that it is possible to reduce the threshold voltage for DNA dissociation by at least factor of 5, since the surface area to volume ratio decreases as 1/R, where R is the particle radius smaller particles possess a greater charge density. In specific terms, given the same relative surface coverage of BSPP, the charge density of a 2 nm nanoparticle is ~28 $C/nm^3$ providing a reduction in the requisite electric field of ~14.

In another aspect, the surface charge density can also be controlled by the preparation of the nanoparticles. In the previous example, the use of BSPP is a convenience for stabilizing the nanoparticle in solution. Other compounds can be selected to achieve a similar effect. For example, the initially prepared nanoparticles can be coated with citrate, thereby giving a higher surface charge and higher charge density. Higher charge densities can be achieved as needed, and can be achieved by selecting an appropriate compound to be included in the preparation of a nanoparticle.

Prior to the present disclosure, available microelectronic technology suffers from the same disadvantage that GENE-CHIP™ technology suffers, namely, the need to individually wire a separate electrode for each sample. Moreover, commercially available NANOCHIP™ devices are pre-wired for either 25 or 100 samples (Feng & Nerenberg, (1999) *Gene Ther. Mol. Biol.* 4: 183-91), but there is no capacity for more or less than 25 or 100 samples. The present invention circumvents this limitation first by eliminating any need for wiring of electrodes, and second, by eliminating restrictions on the number of samples that can be associated with a support.

VII.F. Detection of Analyte Recognition by Antibodies Using a Photoelectrochemistry Approach Representative approaches to the use of photoelectrochemsitry for antibody-analyte detection are set forth here. All of these geometries provide sufficient proximity to the electrode surface that photoinduced electron transfer can reach the surface. Efficient charge flow to the electrode surface can be facilitated by secondary electron acceptors that shuttle electrons to the surface. All three basic strategies involve antibody recognition. For example, recognition of a surface analyte such as a membrane protein, surface attached synthetic product or any other immobilized analyte, via binding of secondary antibodies is provided. Secondary antibodies recognize the primary antibody. For example, a rabbit (primary) antibody can be raised against a particular antigen (analyte) and then a mouse (secondary) antibody raised against the heavy chain of rabbit antibodies can bind to any of the primary antibodies. An advantage of this approach is that it reduces the number of labeling steps required. If the primary antibody is labeled, then each antibody must be labeled. This can be very time consuming. If instead the secondary antibody is labeled, then one generic antibody can be labeled.

In one example, if a target analyte is soluble, a probe, such as an antibody can first be immobilized, for example on a support. A second antibody can be introduced that it is associated with a nanoparticle that comprises a photoredox molecule. This is a standard sandwich assay, in which the target analyte is bound by the first probe and detected by the second.

VII.G. Oligonucleotide Ligation Assay (OLA)-Based Methods

In some applications, it might be desirable to employ a oligonucleotide ligation-based method. OLA-based approaches can employed, for example, when identifying single base mismatches. In one example, when it is desired to detect a mutation in a nucleic acid sequence, an oligonucleotide ligation assay-type approach can be employed. In one OLA-based embodiment of a method of detecting a mutation one or more probe sequences are initially attached to a support. Next, a nucleic acid sequence comprising the probe sequence is exposed to two nucleic acid sequences that are adjacent to each other in the probe sequence. A first nucleic acid sequence can flank the position of a known or suspect mutation in a probe sequence, while a second sequence can overlap the mutation. One of the nucleic sequences can comprise a label, such as a biotin, while the other can be associated with a nanoparticle. The two sequences are hybridized with the probe sequence in the presence of ligase. If the first and second sequences are exactly complementary to the probe, ligation will occur and the ligated product can be isolated using the biotin label and subsequently associated with a nanoparticle. If the sequences are not precisely complementary, no ligation will occur and only the sequence comprising biotin will be isolated.

Following isolation of the ligated (or unligated) product, the product can be contacted with a support comprising a probe, and duplex formation detected. If a nanoparticle is present, a photocurrent will be observed, but if no nanoparticle is present, no current will be observed.

The following is only an example of an OLA-based method. Those of ordinary skill in the art will recognize that modifications of the example method can be made without departing from the spirit and scope of the method. See, e.g., Landegren et al., (1988) *Science* 241: 1077-1080; Nickerson et al., (1990) *Proc. Natl. Acad. Sci. U.S.A.* 87: 8923-8927, U.S. Pat. No. 4,851,331, U.S. Pat. No. 5,185,243, U.S. Pat. No. 5,679,524 and U.S. Pat. No. 5,573,907, WO 94/21820, WO 97/31256, WO 96/41011 and U.S. Pat. No. 5,503,980.

VIII. Advantages Over Known Detection Systems

The methods and compositions of the present invention represent an advance beyond duplex detection methods known in the art. For example, the methods and compositions of the present invention offer a detection advantage. Both the optical and electrochemical methods of detection described herein offer an amplification advantage over current fluorescence microscopy and electrochemical detection methods. For the electrochemical detection methods described in the present invention, a large signal amplification is possible. This is due in part to the fact that a single nanoparticle can carry thousands of secondary components, which can be a source of photoredox molecules. Further, nanoparticles can be employed to prevent non-specific adsorption in surface-based hybridization assays. Non-specific adsorption of fluorescent oligonucleotides is one of the major problems in current microarray technology. Moreover, nanoparticles can provide an alterative means to utilize the high electric fields currently required to desorb mismatched DNA. The high charge density achievable with nanoparticles provides a much stronger electrostatic repulsion from an electrode than for DNA itself.

LABORATORY EXAMPLES

The following Laboratory Examples have been included to illustrate some modes of the invention. Certain aspects of the following Laboratory Examples are described in terms of techniques and procedures found or contemplated by the present inventors to work well in the practice of the invention. These Laboratory Examples are exemplified through the use of standard laboratory practices of the inventors. In light of the present disclosure and the general level of skill in the art, those of skill will appreciate that the following Laboratory Examples are intended to be exemplary only and that numerous changes, modifications and alterations can be employed without departing from the spirit and scope of the invention.

Laboratory Example 1

Generation of DNA-Nanoparticle Complexes and Support-Bound DNA

DNA-nanoparticle conjugates were synthesized to serve as targets of surface-attached DNA oligonucleotide probes. Single-stranded DNA was attached to gold particles having sizes ranging from 5 to 30 nm. Single stranded DNA was attached using methods disclosed herein. Briefly, single stranded DNA was exposed to phosphine, which attached at the 5' terminal end of the DNA sequence. The phosphine-DNA moiety was then subjected to thiol deprotection in the presence of gold particles, whereby the single stranded DNA was bound to the gold particle.

In a separate step, complementary DNA was bound to the surface of a gold support using an alkane thiol linker, C6 mercaptohexanol in accordance with techniques described by Loweth et al., (1999) *Angew. Chem. Int. Edit.* 38: 1808-12, and Storhoff & Mirkin, (1999) *Chem. Rev.* 99: 1849-62. Briefly, solutions of single stranded DNA and C6 mercaptohexanol were prepared. DNA concentrations ranged from 0-20%. Gold support surfaces were then exposed to the DNA-mercaptohexanol solutions for a preselected period of time. Unbound DNA was removed. Following the association of DNA with the support surface, the support surface was passivated by exposure to C6 mercaptohexanol. Surface passivation decreases the potential for the non-specific binding of probe DNA-nanoparticle complexes.

Laboratory Example 2

Characterization of Nanoparticle-Containing DNA Duplexes

Figure 3A:
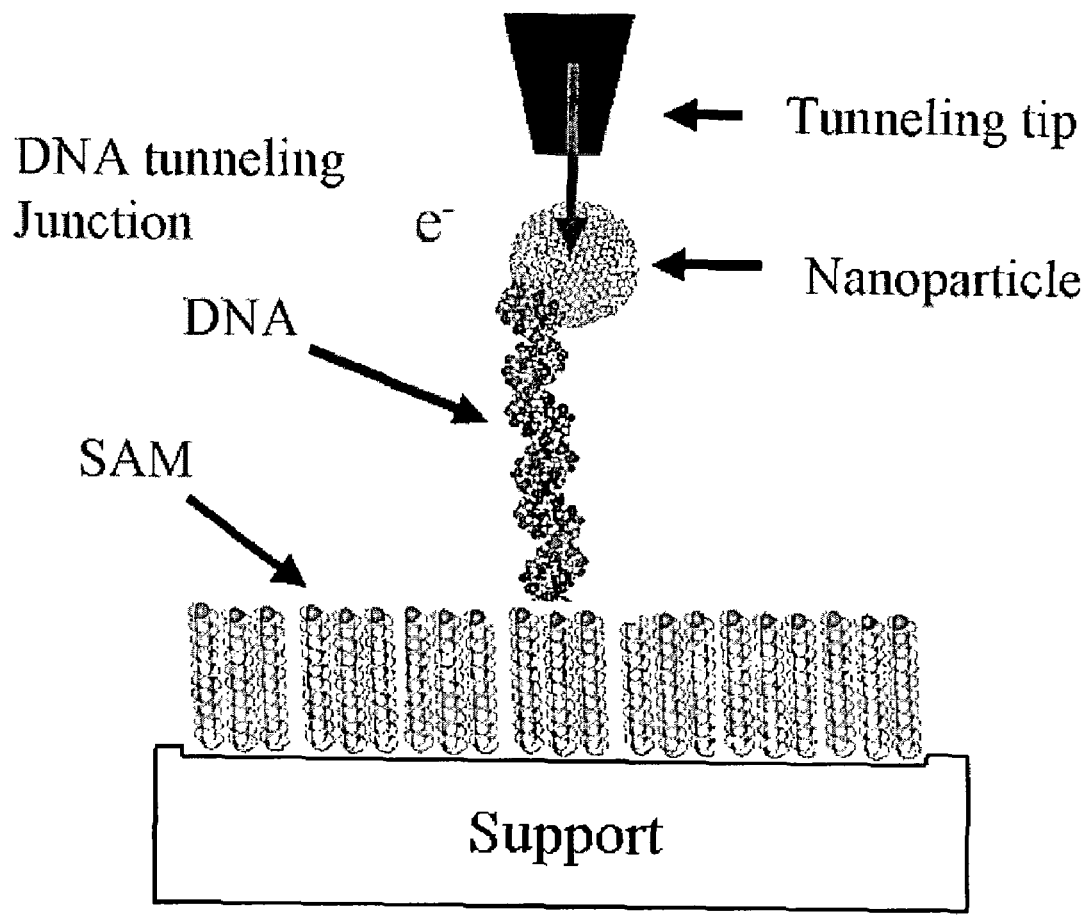
FIG. 3A is a diagram depicting the use of scanning tunneling microscopy (STM) to detect support bound DNA.
Figure 3B:
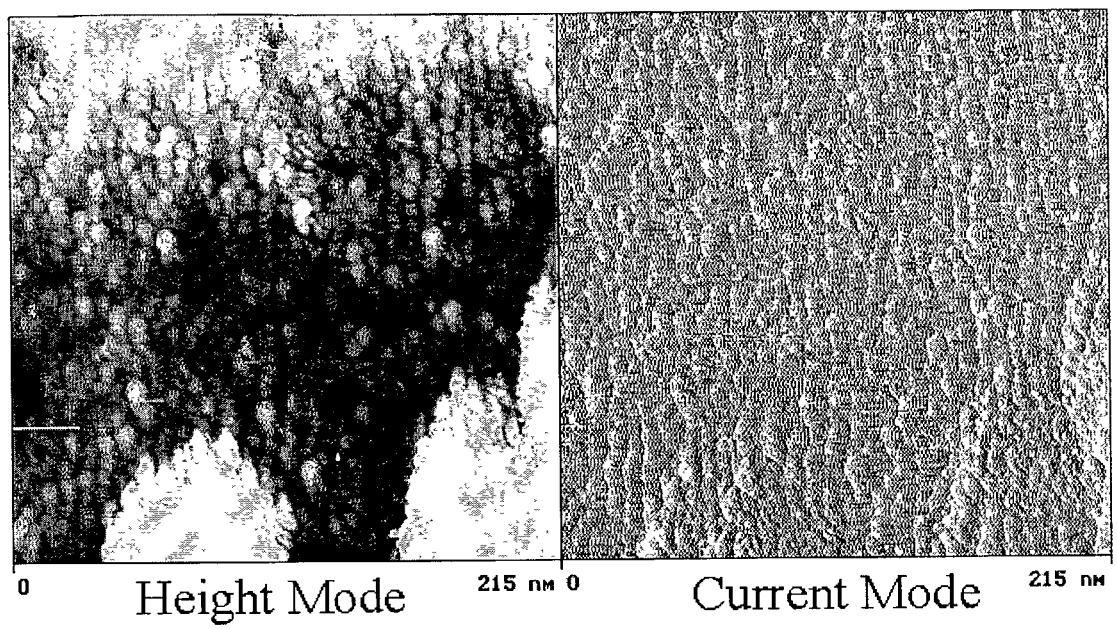
FIG. 3B is an STM image of a 215×215 nm region of a gold support. The region shows duplex formation between surface-bound nucleic acid sequences and nucleic acid probe sequences that contain 5 nm gold nanoparticles, which are recognized by the surface-bound sequences. The lefthand panel shows the image in height mode, while the righthand panel shows the image in current mode.

A height mode scanning tunneling microscopy (STM) image of (surface-bound DNA)-(DNA-nanoparticle) duplexes is shown in the lefthand panel of FIG. 3B. The righthand panel of FIG. 3B is a current mode STM image of the same DNA duplexes depicted in FIG. 3A. The duplexes were formed on the surface of a gold support, and thus demonstrate that duplexes form on a suitable support surface.

Single stranded 31 mer probe DNA sequences were bound to a gold support via reaction with C6 mercaptohexanol as described in Laboratory Example 1. The DNA sequences were commercially prepared using standard nucleic acid synthetic methods. Complementary single stranded target DNA sequences were also prepared synthetically. The target DNA was subsequently bound to nanoparticles 5 nm in size. The scheme by which the nucleic acid targets were bound to nanoparticles is presented in schematic form in FIG. 8. Generally, single stranded DNA was reacted with a phosphine, which associated with the DNA at the 5' end of the sequence to form a phosphine-DNA complex. The complex was subjected to thiol deprotection in the presence of a gold particle to form a DNA-nanoparticle complex. The DNA-nanoparticle complexes were then incubated with the nucleic acid sequences immobilized on the support. Unbound sequences were removed by washing, and the support was examined using STM. A schematic representation of the STM tip and tunneling current are represented schematically in FIG. 3A.

The lefthand panel of FIG. 3B is a 215×215 nm region of the gold support after the hybridization reaction, as visualized with STM. The STM image is presented in height mode, which provides a topographical map of a surface. The nanoparticles bound in the duplexes are visible as spherical representations in the figure. FIG. 3A confirms that DNA duplexes bearing nanoparticles can be clearly visualized by STM. The righthand panel of FIG. 3B is the same image in current, or constant current, mode. In current mode, variations in distance between the STM tip and the surface are monitored and presented as deflections in a constant tunneling current.

Continuing with FIG. 3B, aggregates of nanoparticles and surface defects can both be detected quite readily. Surface defects are identified as the white features that are significantly higher than the average of 15 nm in obtained height mode (lefthand panel of FIG. 3B). The STM images in the left and righthand panels of FIG. 3B illustrate the ability to differentiate between artifacts due to aggregation using surface sensitive techniques. These techniques can be valuable tools in the optimization of surface coverage and the effects of passivating layers.

Laboratory Example 3

Development of Experimental Controls

Controls were developed and employed to ensure that the nanoparticles were localized to single stranded DNA bound on the surface of the support, concurrent with the formation of DNA duplexes. Controls are helpful to show a lack of binding when a component of the system (e.g. surface-bound single stranded DNA, gold particles with single stranded DNA bound) is absent. The STM images presented in FIGS. 4A-4C show there is no adsorption of DNA-nanoparticle conjugates on surfaces where non-complementary DNA, no DNA, or only C-6 hydroxy thiols are present.

Laboratory Example 3.1

Figure 4A:
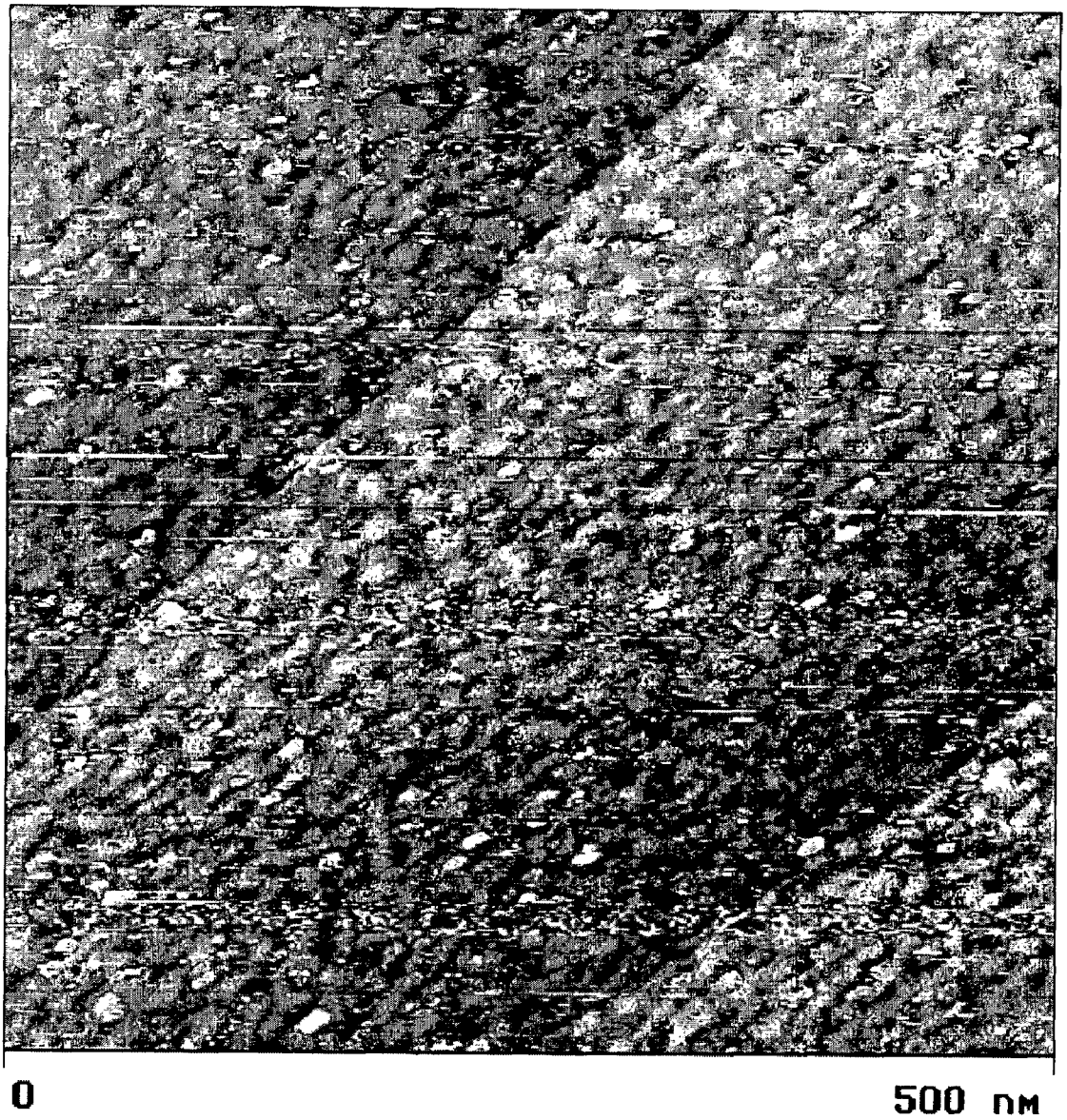
FIG. 4A is an STM image of a 500×500 nm region of a bare gold support (a gold support with no nucleic acids bound to the support), following exposure to nanoparticle-comprising probe sequences. The image is presented in height mode.
Figure 4B:
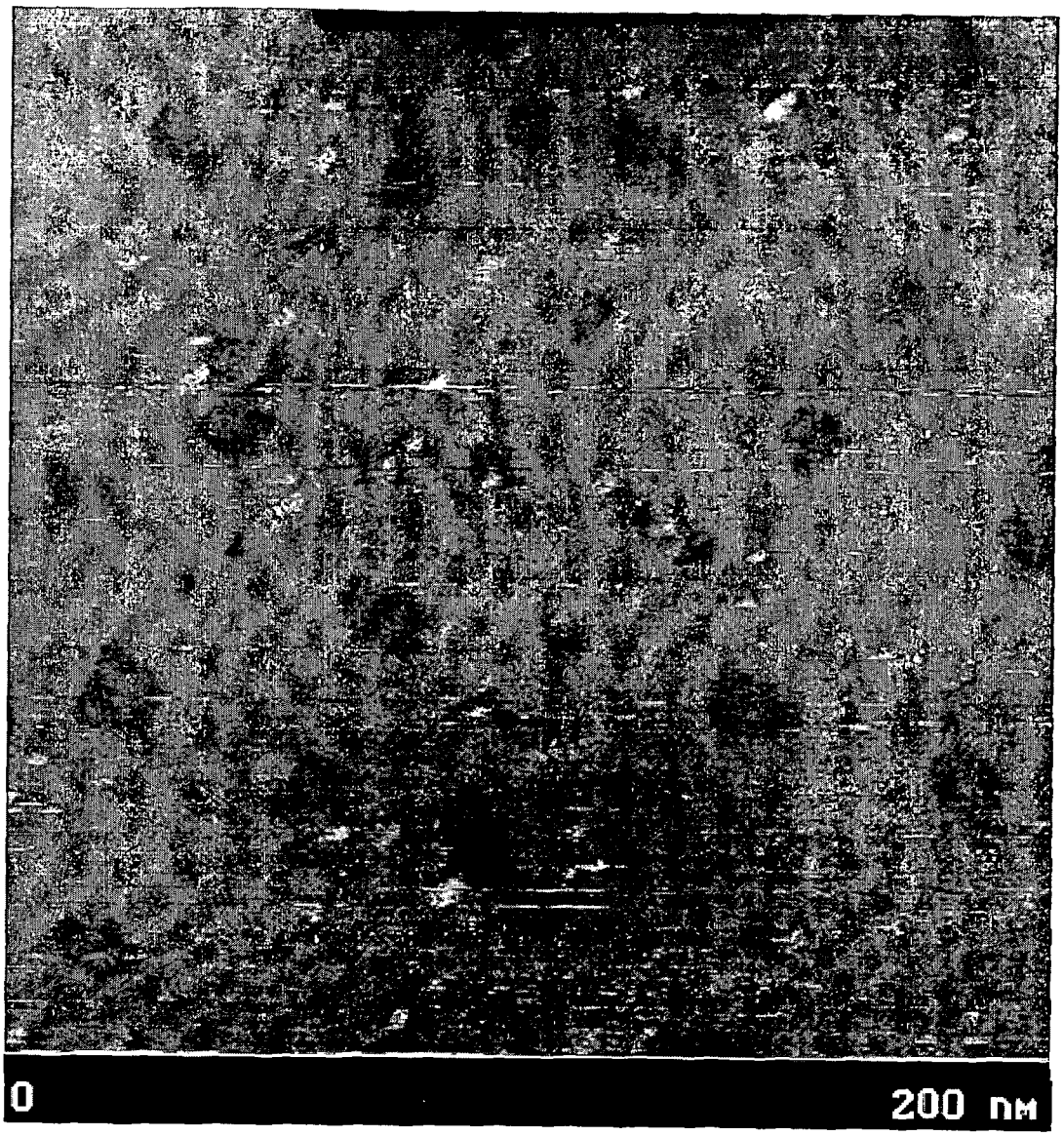
FIG. 4B is an STM image of a 500×500 nm region of a gold support that has been passivated with 6 mercapto-1-hexanol immersed in a phosphine-coated nanoparticle solution. The image is presented in height mode.
Figure 4C:
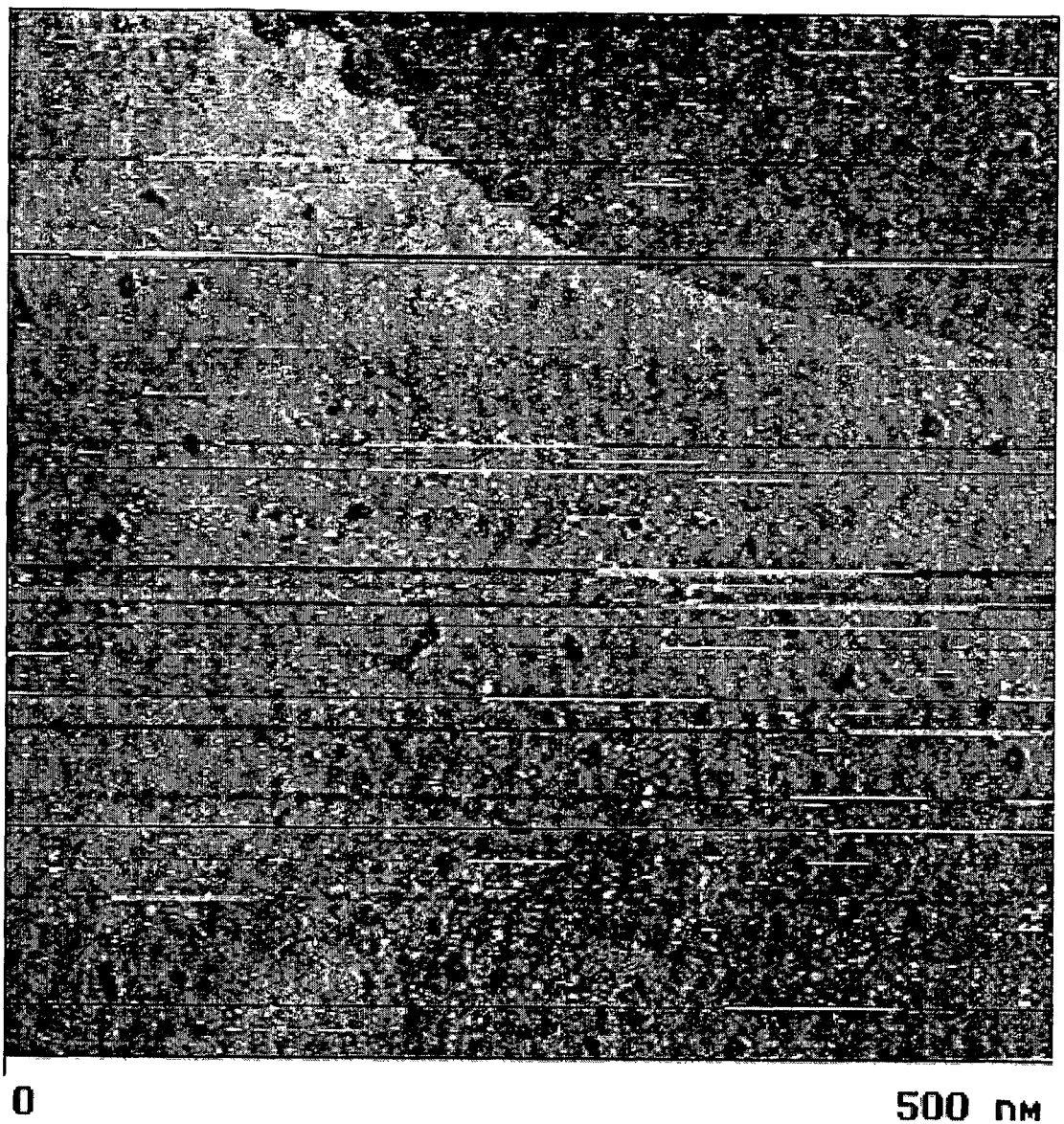
FIG. 4C is an STM image of a 500×500 nm region of a gold support derivatized with single stranded DNA and 6-mercapto-1-hexanol exposed to a solution of phosphine-coated nanoparticles, which is the effective equivalent of non-complementary DNA.

The STM image shown in FIG. 4A was generated using DNA oligomers 31 bases in length (probe and target) that are about 25% complementary. No DNA was bound to the surface of the gold support. Phosphine-coated nanoparticle-DNA complexes were exposed to the bare gold support and non-binding complexes were removed. The support was then examined using STM. The STM image shown in FIG. 4A indicates that there was negligible binding of nanoparticle complexes to the surface.

The STM image shown in FIG. 4A indicates that the use of nanoparticles can eliminate the false positives that typically complicate the interpretation of DNA microarray data. FIG. 4A shows that absent complementary DNA, a nanoparticle-DNA structure will not bind the support. FIG. 4A shows the substantial absence of nanoparticle-containing structures, in that bare gold grains are seen.

Laboratory Example 3.2

The STM image presented in FIG. 4B depicts the surface of a gold support that was passivated by exposure to C6 mercaptohexanol. No single stranded DNA was included in the reaction mixture. Passivation is a method in which a surface is coated with a moiety having the ability to block subsequent binding to the surface at points where the moiety is bound. The surfaces were subsequently immersed in a solution of phosphine-coated nanoparticle-DNA complexes. FIG. 4B shows that there is negligible adsorption of nanoparticle-DNA complexes when only C6 hydroxythiols are present on the surface of a support.

In this example, a gold support surface was passivated by exposure to C6 mercaptohexanol, thereby coating the surface of the support with, essentially, a monolayer of hydroxyl groups. The surface was then exposed to phosphine-coated nanoparticle-DNA complexes and examined using STM.

The STM image depicted in FIG. 4B shows that absent complementary DNA, nanoparticle-DNA complexes will not bind to the support surface. This result indicates that the false positive binding events that can hinder the use of DNA microarrays can be avoided through the use of nanoparticle-based methods.

Laboratory Example 3.3

The STM image presented in FIG. 4C depicts the surface of a gold support to which single stranded DNA was bound. At points where no DNA bound, the surface was passivated by C6 mercaptohexanol. The surface was then exposed to nanoparticle-DNA complexes and examined by STM.

In this example, four different solutions were prepared. Solutions containing 0, 5, 10 and 20% of single stranded DNA, diluted with a solution of C6 mercaptohexanol, were prepared. Gold surfaces were exposed to the 4 solutions for identical periods of time. The surfaces were then exposed to DNA-nanoparticles for identical periods of time.

The STM image depicted in FIG. 4C shows that surfaces presenting non-complementary DNA are not recognized by nanoparticle-DNA complexes.

Laboratory Example 4

Optimization of Nanoparticle Size

Experiments were performed to determine an optimal size for an effective nanoparticle. STM analysis indicates that smaller nanoparticles form more dense monolayers on the surface of a support.

DNA-nanoparticle complexes having sizes of 5 nm and 10 nm were formed as disclosed in Laboratory Example 1. Complementary target DNA was then bound to C6 mercaptohexanol, which was subsequently anchored to the surface of a gold support via a six carbon tether, bound mercaptohexanol. DNA-nanoparticle complexes comprising complementary DNA were then exposed to the DNA anchored to the gold support surface. STM was used to examine the resulting surface-bound duplexes.

Figure 5A:
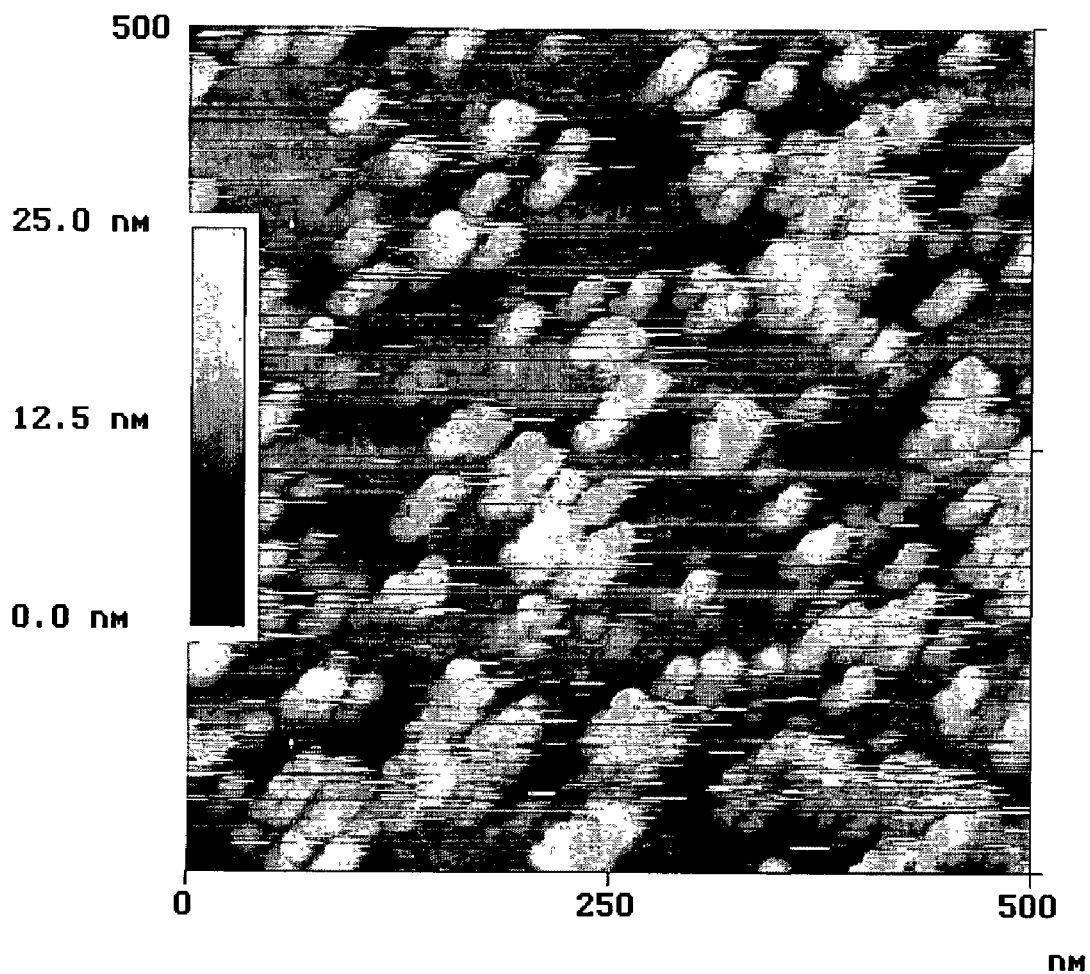
FIG. 5A is an STM image of a 10 nm nanoparticle monolayer of DNA.
Figure 5B:
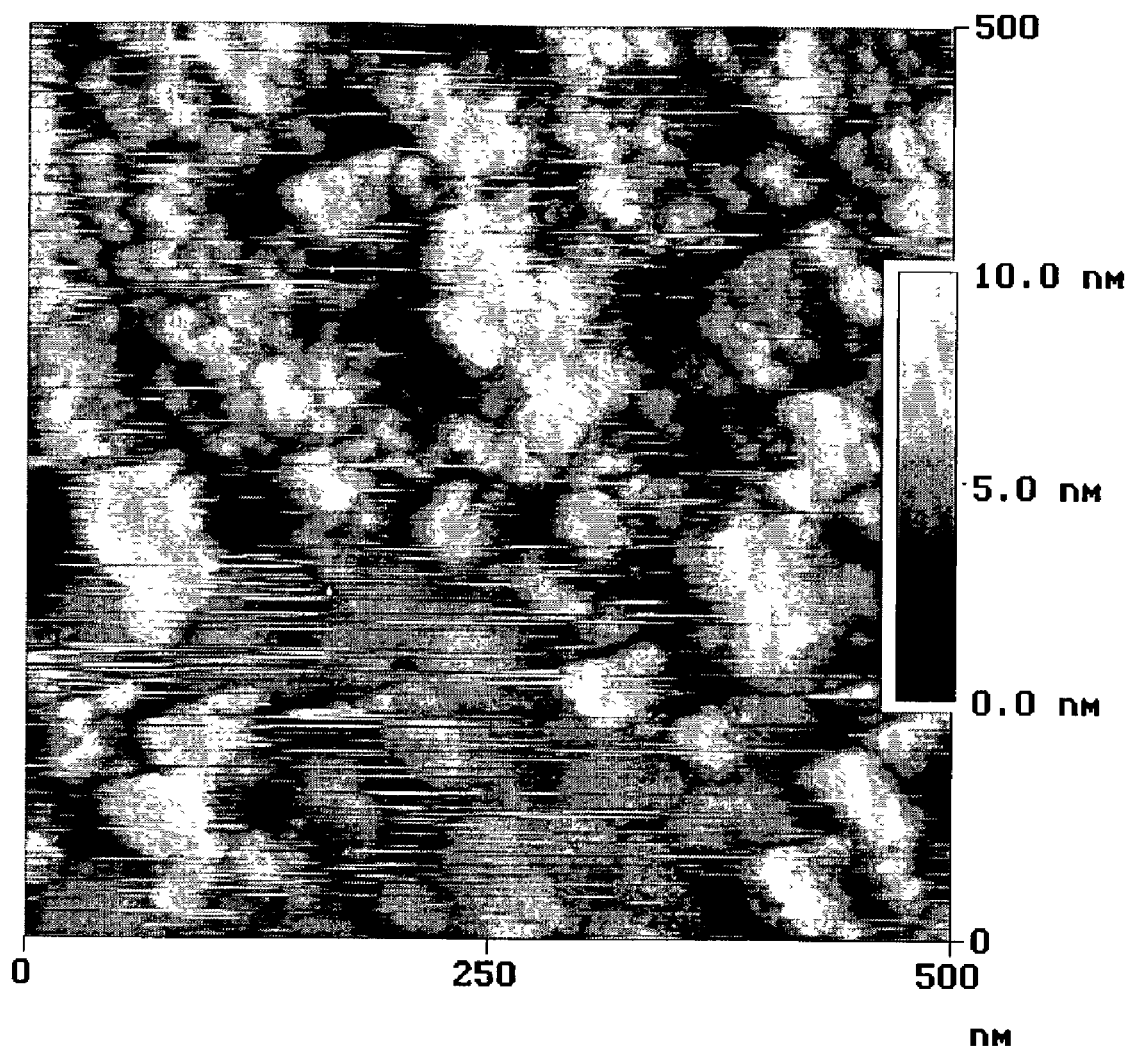
FIG. 5B is an STM image of a 5 nm nanoparticle monolayer of DNA.

As depicted in the STM image in FIG. 5A, the duplexes comprising the larger 10 nm DNA-nanoparticle complexes are spaced apart from one another. In contrast, the STM image depicted in FIG. 5B indicates that DNA-nanoparticle complexes comprising the smaller 5 nm DNA-nanoparticle complexes are more densely packed on the surface of the support.

Laboratory Example 5

Electrochemical Detection of Duplexes

The electrochemistry of ferrocene has been characterized. See, e.g., Uosaki et al., (1991) *Langmuir* 7: 1510; Chidsey et al., (1990) *J. Am. Chem. Soc.* 112: 4301; Tender et al., (1994) *Anal. Chem.* 66: 3173. Thus, ferrocene was selected for use as a secondary component. Ferrocene was modified with a C6 thio-linker and was used as the electroactive species.

Two different samples were prepared. In the first sample, DNA-nanoparticle monolayers were synthesized and bound to a gold support surface as described in Laboratory Example 1. The support surface was passivated using C6 mercaptohexanol to minimize the potential for nonspecific binding. DNA-nanoparticle complexes were incubated with the support-bound DNA to form duplexes. In the second sample, single stranded DNA was bound to a gold support; however, the surface-bound DNA was not exposed to DNA-nanoparticle complexes.

Both samples were exposed to a solution of ferrocene for one minute and then thoroughly rinsed to remove excess unbound ferrocene. The gold surface was completely oxidized with thiols, making the only possible binding site for ferrocene on the nanoparticles themselves. Electrochemical detection of ferrocene on the gold surface was expected to indicate the presence of nanoparticles bound to the surface.

Figure 6:
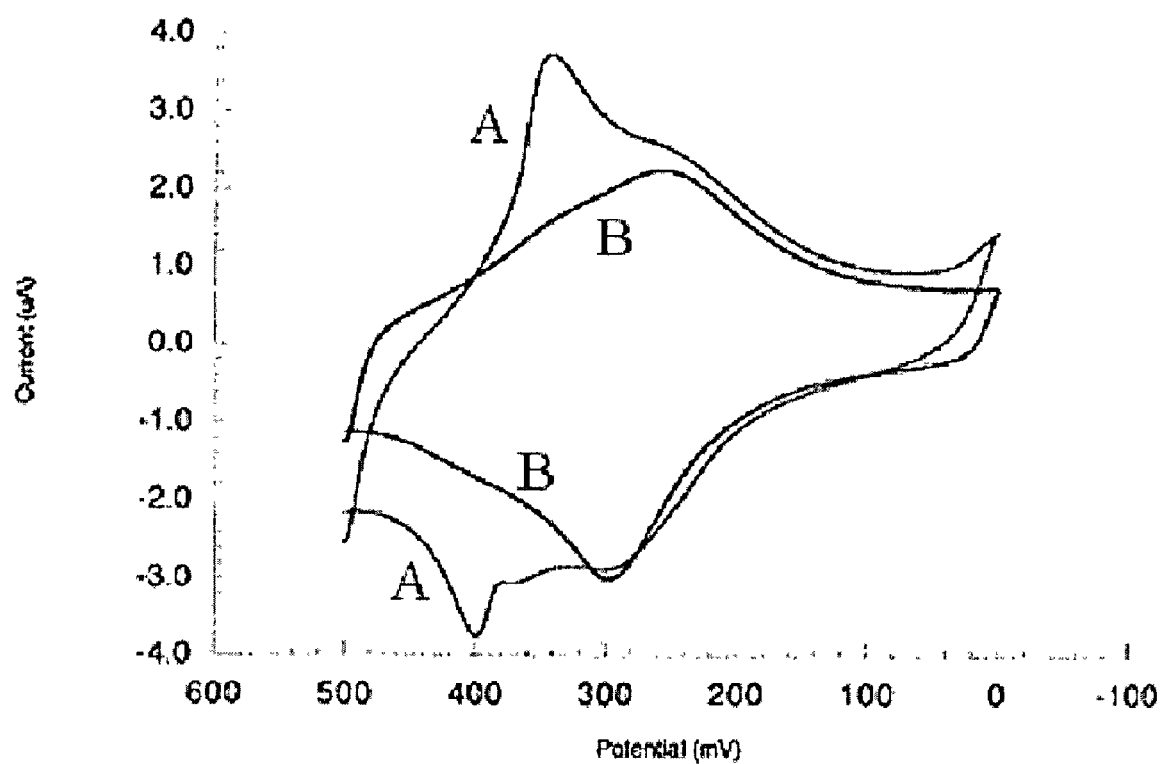
FIG. 6 presents two overlayed cyclic voltammetry traces of a DNA-nanoparticle monolayer (A) and a single stranded DNA monolayer (B).

The results, depicted in FIG. 6, showed an interestingly different electrochemical signature between samples with nanoparticles bound to the surface (Trace A in FIG. 6) and samples without any particles attached to the surface (Trace B in FIG. 6).

These results indicate that electrochemistry is a valuable characterization tool for DNA-nanoparticle monolayers. Of particular note is the ability of electrochemistry to quantify the number of nanoparticles bound to the surface and therefore to estimate the proportion of hybridized DNA strands.

Laboratory Example 6

Optical Spectroscopy

Figure 7:
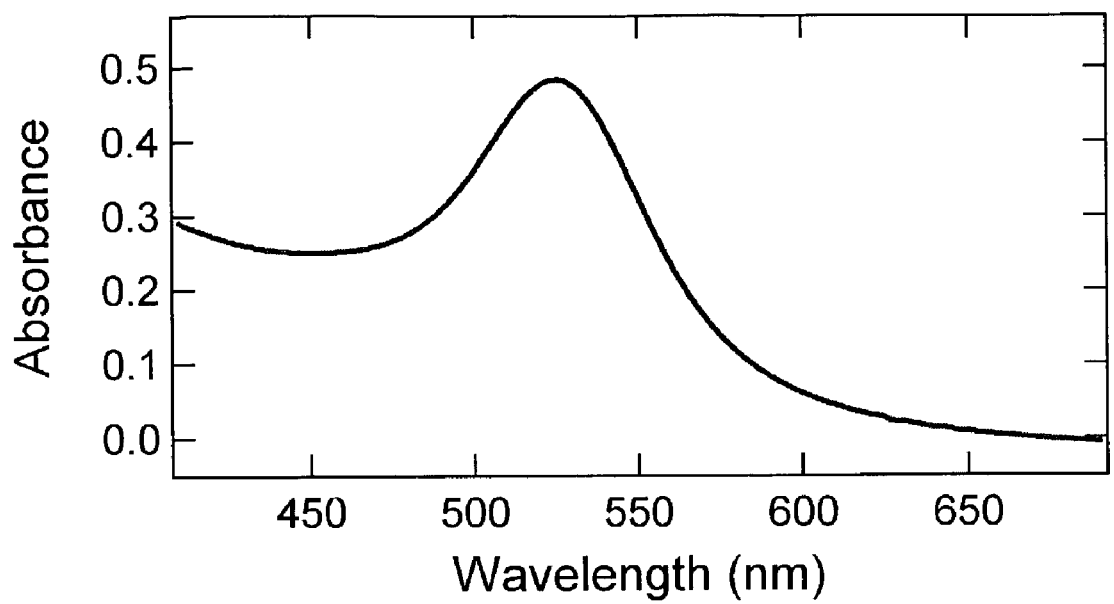
FIG. 7 is an absorption spectrum of a 1 nM solution of 30 nm nanoparticles in a 1 cm pathlength cell.

The absorption of solutions of 5-100 nm DNA-nanoparticle complexes was investigated and found to be quite similar. FIG. 7 depicts the absorption spectrum of a 1 nM solution of 30 nm DNA-nanoparticle complexes in a 1 cm pathlength cell. Using Beer's law, the extinction coefficient was found to be $5 \times 10^8$ $M^{-1}$ $cm^{-1}$.

The complexes are intensely colored due to the plasmon resonance band. The plasmon resonance band results from a collective oscillation of the electrons in the metal. The frequency of the band depends on the size of the nanoparticle, since the scattering lengths of electrons are longer than the particle size at room temperature. The plasmon band is surprisingly intense. The extinction coefficient is estimated at greater than $10^8$ $M^{-1}$ $cm^{-1}$. This is shown in the absorption spectrum of 30 nm nanoparticles in FIG. 7. The intense absorption band of metal-based nanoparticles is useful for detection purposes.

Laboratory Example 7

Photoelectrochemical System

The photoelectrochemical (PEC) system described in this Laboratory Example for DNA hybridization detection employs a series of Au—S bonds. Other experimental details of the setup were studied, including the sacrificial electron donor within the photoelectrochemical system and its concentration as well as the voltage range which is non-destructive for the working electrode (modified Au substrate).

Materials and Methods for Laboratory Example 7

Chemicals

All chemicals were used as received from vendors without further purification. Triethanolamine, tripropylamine, and triethylamine were supplied by Aldrich Chemical Co. of Milwaukee, Wis. Fisher Scientific (Pittsburgh, Pa.) supplied disodium ethylenediaminetetraacetic acid. Mallinckrodt (Phillipsburg, N.J.) supplied potassium phosphate monobasic.

Cyclic Voltammetry

An EG&G Princeton Applied Research Potentiostat/Galvanostat Model 273A equipped with EG&G Instruments, Inc. Model 270/250 Research Electrochemistry Software 00 was used for all electrochemical measurements (available from EG&G Princeton Applied Research or Princeton, N.J.). Cyclic voltammetry was used for the characterization of the electron donor using a 0.071 $cm^2$ gold working electrode, a Pt counter electrode, and a Ag/AgCl reference electrode at a scan rate of 100 mV/s. The electrolyte was 0.1M aqueous potassium phosphate (pH 7.2). The sample was purged for 15 minutes with nitrogen before analysis. The potential was scanned from 0 to 1V vs Ag/AgCl. The oxidative stripping potential of thiol on a gold surface was also investigated to determine a non-destructive potential range for photoelectrochemical measurements. The potential was cycled multiple times from 0 to 1.7V vs. Ag/AgCl with a Pt counter electrode.

Photoelectrochemistry

The light source for the photoelectrochemical measurement was a Oriel Instruments 75 W Xenon arc lamp operated using an Oriel 68806 Basic Power Supply (50-200 W), available from Thermo Oriel of Stratford, Conn. The photoelectrochemical cell was connected to an EG&G Princeton Applied Research Potentiostat/Galvanostat Model 273A equipped with EG&G Instruments, Inc. Model 270/250 Research Electrochemistry Software 00. The diagram for the experimental setup is in Figure The optical window and working electrode each have an area 0.38 cm². The working electrode was irradiated with a light intensity of 0.64 W/cm². The electrolyte was composed of 0.1 M KP buffer (pH 7.2).

Results of Laboratory Example 7

Photoelectrochemical Light and Dark Background Currents

Many factors can be considered when designing a dye-sensitized photoelectrochemical system, such as the dye, the sacrificial electron donor, and the potential at which the experiments will be performed. The dye used in the present Laboratory Example was $[Ru(bpy)_3]^{2+}$. The following describes the selection of an electron donor as well as focuses on the potential window in which the PEC experiments may be performed. Both parameters play a role in optimizing the experimental conditions.

In the photoelectrochemical system of the present Laboratory Example, the working electrode, which is the DNA-modified gold substrate, was held at a constant potential and the current monitored. The dark current is defined as the current when the sample is not being illuminated by the Xe arc lamp. Upon illumination, the anodic current increases due to photoexcitation. The photocurrent ($I_{PC}$) is defined in the following equation.

$$I_{PC} = I_{light\ on} - I_{light\ off}$$

The sacrifical electron donor of the PEC system was investigated in order to obtain a low dark current. Due to their common use in chemiluminescent and PEC systems for $[Ru(bpy)_3]^{2+}$, disodium ethylenediaminetetraacetic acid (EDTA), triethanolamine (TEOA), triethylamine (TEA), and tripropylamine (TPA) were tested. If the oxidation potential of the electron donor is less than the potential used in the PEC experiments, the electron donor at the electrode surface will undergo a oxidation causing an increased anodic current. Due to the high concentration of donor (50 mM), it can take hours for the dark current to decrease while at a constant potential.

Cyclic voltammetry was used to monitor the reduction potential of disodium ethylenediaminetetraacetic acid (EDTA), triethanolamine (TEOA), triethylamine (TEA), and tripropylamine (TPA). Tertiary amines undergo two oxidations as shown in the following equations, using TPA as an example, with the second oxidation being irreversible.

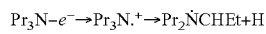

The data showed that the first oxidation of TPA starting at a potential lower that 0V, TEA at approximately 0V, and TEOA around 0.25V vs. Ag/AgCl. These three molecules yield a high dark current when working in a potential range of 0.25V to 0.65V. EDTA oxidation starts at 0.75V, which allows it to retain a low dark current up to this potential. FIG. 8 demonstrates this improvement in dark current by comparing TEOA and EDTA. The potential was held at 0.5V vs. Ag/AgCl with the modified electrode comprising dsDNA—10 nm Au colloid—$[Ru(bpy)_3]^{2+}$. The dark current of the TEOA is ~750 nA after 25 seconds while that of EDTA falls to less than 100 nA within the first second. EDTA was used as the sacrificial electron donor in the following experiments.

Using EDTA as an electron donor allows a working potential range of 0 to 0.75V vs. Ag/AgCl, however, at high potentials the thiol monolayer is destroyed due to oxidative desorption from the gold substrate. The equation for thiol desorption is as follows

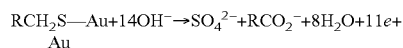

Figure 10:
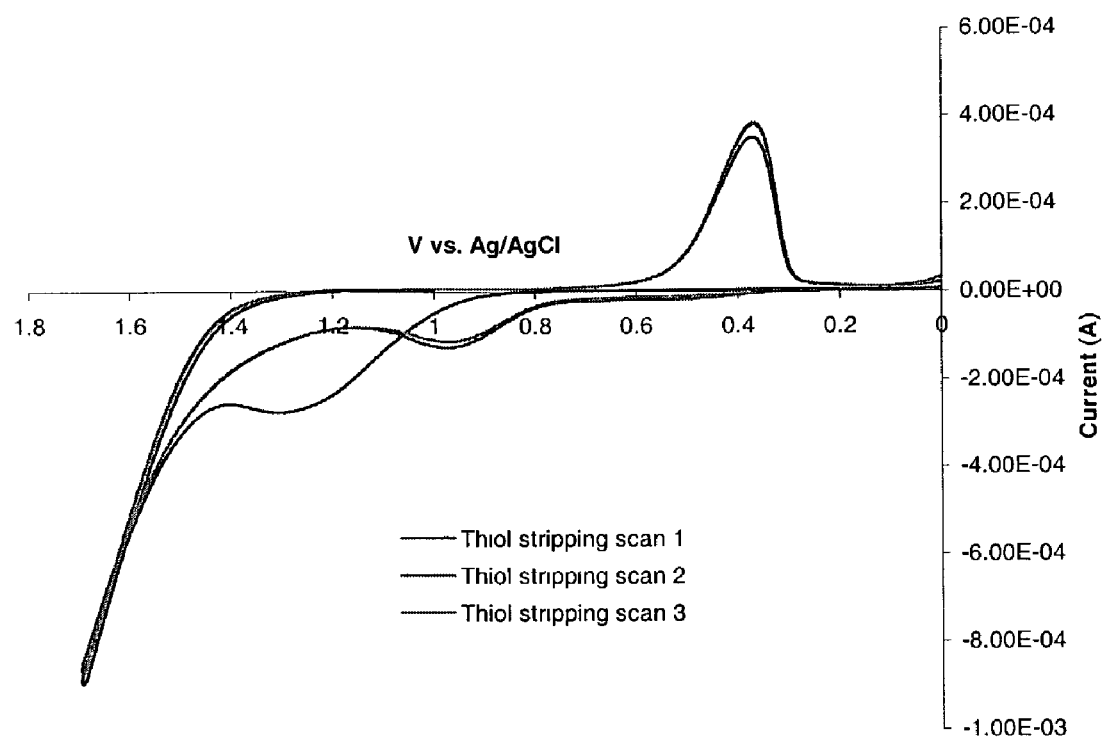
FIG. 10 is a plot depicting the results of a thiol desorption operation.

A 20% probe monolayer was tested in order to determine the potential at which thiol desorbs. This desorption has previously been reported at a potential just above 0.75V vs. SCE in a 0.15M phosphate buffer (pH 7.5) (Zu & Bard, (2001) *Anal. Chem.* 73: 3960-396). FIG. 10 shows the thiol stripping results from the 20% probe monolayer in 0.1M KP buffer (pH 7.2). The potential was cycled 3 times. The first cycle shows oxidative thiol desorption starting at 0.8V vs. Ag/AgCl, which is in close agreement with previous results. The cathodic peak observed is the reductive gold oxide stripping. The second and third scans resulted in anodic formation and reductive stripping of gold oxide.

Figure 11:
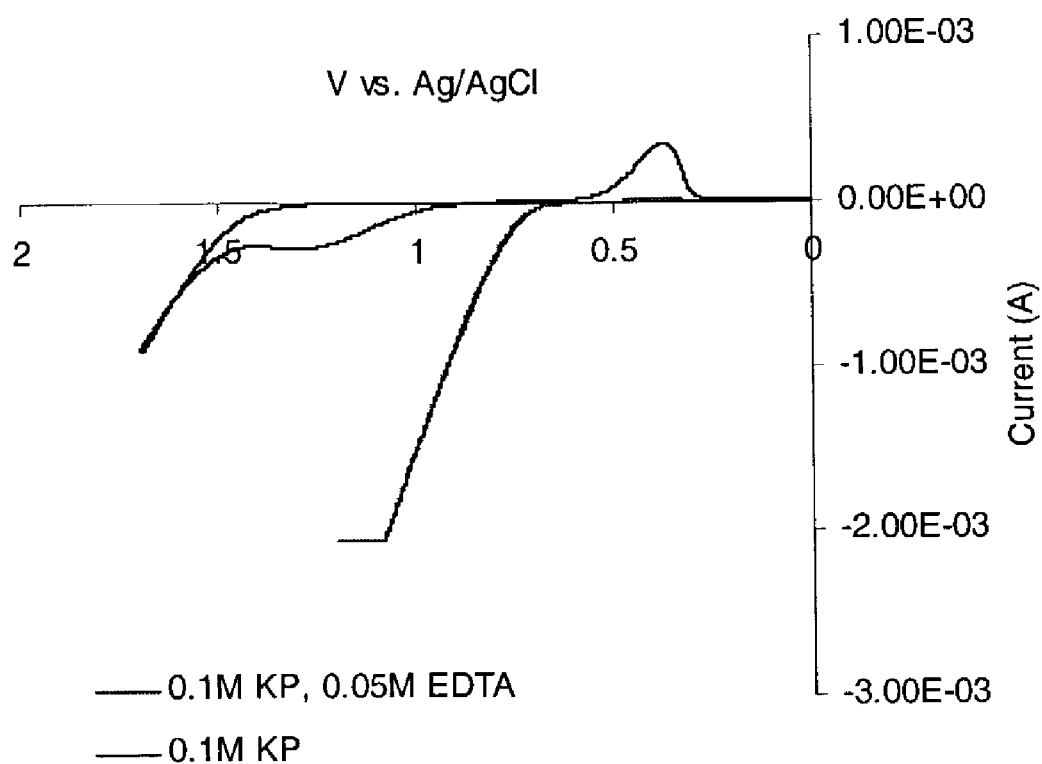
FIG. 11 is a plot depicting the results of a thiol desorption in the presence of EDTA.

Thiol desorption was also attempted in the 0.1M KP buffer with 0.05M EDTA (FIG. 11). The thiol desorption peak was not visible above the oxidative current of EDTA and only a small gold oxide reduction peak was visible in the cathodic current. According to the lack of gold oxide stripping it appeared that the thiol layer was not being destroyed even after numerous cycles. For this monolayer the electrolyte solution was switched back to 0.1M KP buffer without EDTA, and thiol desorption was observed. Due to the high concentration of EDTA a competition for electrons might have been present with more electrons being donated to EDTA rather than the oxidation process of thiol desorption.

Control Experiments

After hybridization the modified gold substrate was placed in a 1 mM aqueous solution on the thiolated $[Ru(bpy)_3]^{2+}$ for four hours for the molecule to chemisorb to the Au colloids. This molecule contains a thioacetate, rather than a thiol. While a thiol will adsorb to a gold substrate within seconds, it often takes hours for the thioacetate to form a Au—S bond due to the acetyl-protecting group. This long deposition time was given consideration, due to the possibility of the thiol displacement on the surface of the gold, i.e., the thiolated $[Ru(bpy)_3]^{2+}$ displacing the mercaptohexanol (MCH) or DNA. Control experiments were performed in order to investigate this issue.

Figure 12:
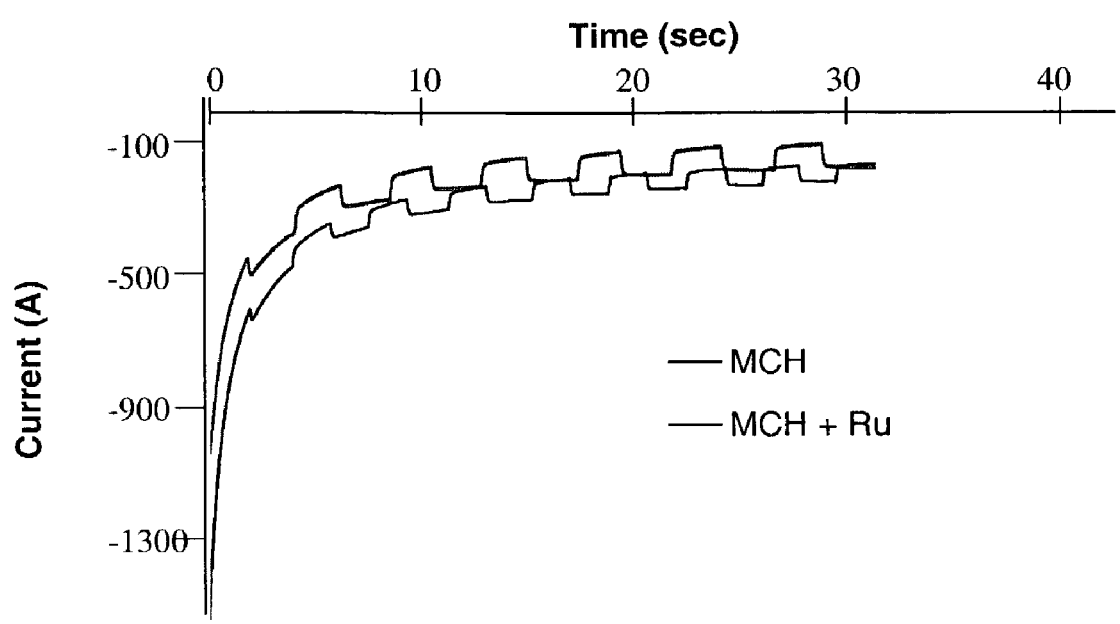
FIG. 12 is a plot depicting a first [Ru(bpy)$_3$]$^{2+}$ deposition control.

In order to determine if displacement was occurring a 100% MCH monolayer was exposed to the $[Ru(bpy)_3]^{2+}$ molecule for four hours. The PEC data is shown in FIG. 12. TEOA was used as the electron donor in this PEC system, which is the cause of the dark current variation. The results showed unexpectedly that a MCH monolayer produces a photocurrent of about 50 nA. A very slight decrease in photocurrent was observed after the modified Au substrate was exposed to the $[Ru(bpy)_3]^{2+}$ molecule.

Figure 13:
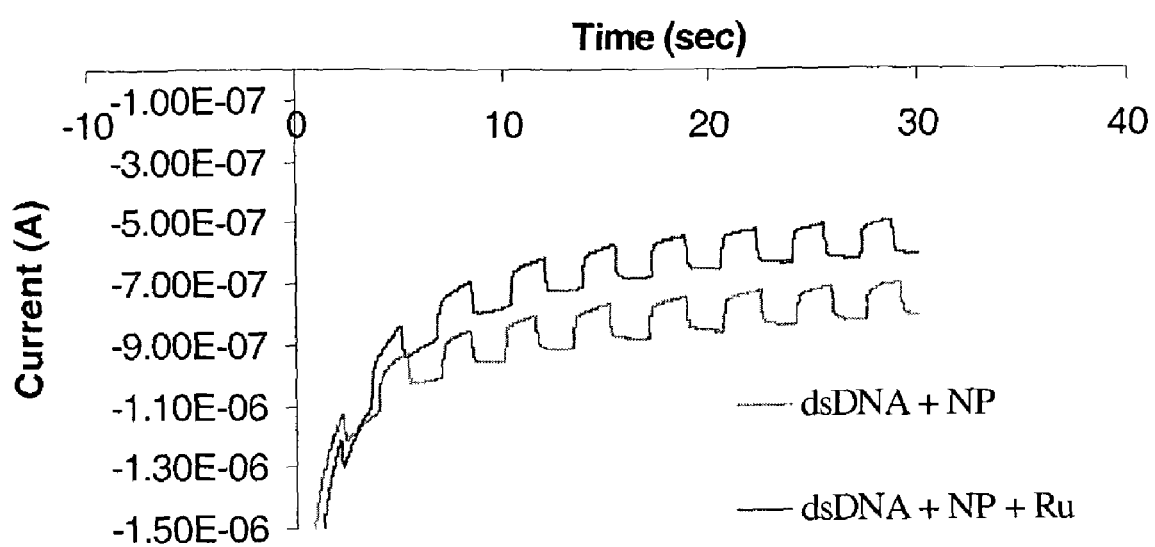
FIG. 13 is a plot depicting a second [Ru(bpy)$_3$]$^{2+}$ deposition control.

A second control was used to help confirm that the monolayer thiol was not being displaced. In the target preparation, a non-thiolated target oligo was mixed with the Au colloid. Since the oligo did not contain a thiol it should not bond with the colloid resulting in free oligo in solution with Au colloid. A probe substrate was hybridized in this solution and then exposed to the thiolated [Ru(bpy)$_3$]$^{2+}$. The target was expected to hybridize resulting in dsDNA, however, the Au colloid should stay in solution and rinsed away before [Ru(bpy)$_3$]$^{2+}$ deposition. The PEC results in FIG. 13 show virtually no change in photocurrent for the dsDNA after exposure to the thiolated [Ru(bpy)$_3$]$^{2+}$. Again, the variation in dark current is due to the use of TEOA as the electron donor in the PEC system.

It was found that the 20% probe/80% MCH monolayer produces a photocurrent of approximately 40 nA. This photocurrent appears to be a result of MCH since the bare gold electrode does not produce a photocurrent and the photocurrent was present with a 100% MCH monolayer. A slight increase in photocurrent was noted after the probe was hybridized in a 1 nM target solution (target attached to Au colloid via Au—S bond) before the thiolated [Ru(bpy)$_3$]$^{2+}$ was added. A large increase in photocurrent is observed after the thiolated [Ru(bpy)$_3$]$^{2+}$ is attached to the gold nanoparticle.

Oligonucleotide Detection

This section presents the photoelectrochemical detection of DNA hybridization using the dye-sensitizing molecule [Ru(bpy)$_3$]$^{2+}$. The PEC response from this system is effected by the applied potential as well as the concentration of [Ru(bpy)$_3$]$^{2+}$. The concentration of the dye is directly related to the amount of target that hybridizes.

Figure 14:
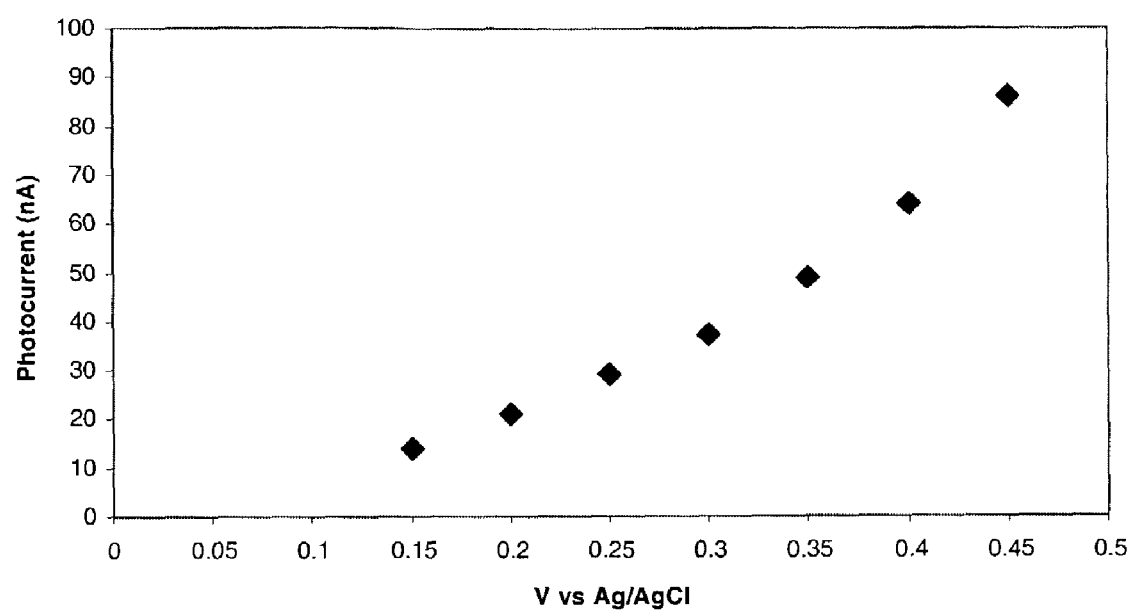
FIG. 14 is a plot of photocurrent versus potential in a photoelectrochemical detection system.

A 20% probe oligo on gold substrate was prepared as described herein and hybridized to the target oligo—Au colloid that was at a concentration of 10 nM. This sample was used to monitor the effect of applied potential on photocurrent. The potential was held in a range from 0.1V to 0.5V vs. Ag/AgCl with the light chopped at 0.5 Hz. $I_{PC}$ was plotted against potential in FIG. 14. An exponential increase in photocurrent was observed with increasing potential up to 0.5V.

A calibration curve was created by hybridizing a probe substrate in target solutions concentrations varying from 0.5 nM to 10 nM.

REFERENCES

The references listed below as well as all references cited in the specification are incorporated herein by reference to the extent that they supplement, explain, provide a background for or teach methodology, techniques and/or compositions employed herein.

Alvarez et al., (1997) *J. Chem. Phys. B* 101: 3706
Beier & Hoheisel (2000) *Nucl. Acids. Res.* 28(4): e11
Bowtell, (1999) *Nature Genet. Supplement* 21: 25-32
Bulyk et al., (1999) *Nat. Biotechnol.* 6: 573-7
Chee et al., (1996) *Science* 274: 610-13
Chen & Huang, (2000) *Langmuir* 16: 2014
Cheung et al., (1999) *Nature Genet. Supplement* 21:15-19
Chidsey et al., (1990) *J. Am. Chem. Soc.* 112: 4301
Dubiley et al., (1997) *Nucleic Acids Res.* 25: 2259-2265
Duggan et al., (1999) *Nature Genet. Supplement* 21: 10-14
Eisen & Brown, (1999) *Method Enzymol.* 303: 179-205
Elghanian et al., (1997) *Science* 277: 1078
Enustun & Turkevich, (1963) *J. Am. Chem. Soc.* 85:3317
Feng & Nerenberg, (1999) *Gene Ther. Mol. Biol.* 4: 183-91
Ferguson et al., (1996) *Nature Biotechnol.* 14: 1680-1684
Gilles et al., (1999) *Nature Biotechnol.* 17: 365
Hacia, (1999) *Nature Genet. Supplement* 21:42-47
Halushka et al., (1999) *Nat. Genet.* 22: 239-47
Harrington et al., (2000) *Curr. Opin. Microbiol.* 3: 285
Hayashi, (1987) *J. Vac. Sci. Technol. A*5(4): 1375-84;
Hayashi, (1987) *Phys. Today*, December 1987, 44-60
Heller et al., (2000) *Electrophoresis* 21: 157
Koide et al., (1999) *Thin Solid Films* 350: 223-227
Landegren et al., (1988) *Science* 241: 1077-1080
Lipschutz et al., (1999) *Nat. Genet. Supplement* 21: 20-24
Lockhart et al., (1996) *Nature Biotechnol.* 14: 1675-1680
Lockhart & Winzeler, (2000) *Nature* 405: 827-36
Loweth et al., (1999) *Angew. Chem. Int. Edit.* 38: 1808-12
Marinakos et al., (1998) *Chem. Mater.* 10:1214-19
Marinakos et al., (1999) *Adv. Mater.* 11:34
Martin, (1994) in *The Polymerase Chain Reaction* (Mullis, Ferre & Gibbs, eds.), pp. 406-17. Berkhauser, Boston
Michael et al., (1998) *Anal. Chem.* 70:1242-1248
*MRS Bulletin*, January 1990, pgs. 16-47
Nickerson et al., (1990) *Proc. Natl. Acad. Sci. U.S.A.* 87: 8923-8927
Nuovo et al., (1999) *J. Histol. Cytochem.* 47:273-279
Pirrung, (1997) *Chem. Rev.* 97: 473-486
Qingwen et al., (2000) *Analyst* (Cambridge, United Kingdom) 125: 1908-1910
Rockett & Dix, (1999) *Environ. Health Persp.* 107: 681-85
Sambrook et al., (1992) *Molecular Cloning: A Laboratory Manual*, Cold Spring Harbor, N.Y.
Schena et al., (1995) *Science* 270: 467-470
Schena (ed.), (2000) *Microarray Biochip Technology*, Eaton Publishing, Natick, Mass.
Singh-Gasson et al., (1999) *Nature Biotechnol.* 17:974-978
Spargo et al., (1993) *Mol. Cell. Probe* 7: 395-404
Stewart, (2000) *Genome Res.* 10:1-3
Storhoff & Mirkin, (1999) *Chem. Rev.* 99: 1849-62
Storhoff et al., (1998) *J. Am. Chem. Soc.* 120: 1959
Swanson et al., (2000) *Sensor Actuat. B-Chem.* 64: 22
Taton et al., (2000) *Science* 289:1757-1760
Tender et al., (1994) *Anal. Chem.* 66: 3173
Uosaki et al., (1991) *Langmuir* 7: 1510
Vrana et al., (2001) "Microarrays and Related Technologies: Miniaturization and Acceleration of Genomic Research", Cambridge Healthtech Institute Report, May 8, 2001.
Yamada et al., (1997) *J. Electroanal. Chem.* 426: 23-26
Yershov et al., (1996) *Proc. Natl. Acad. Sci. U.S.A.* 93:4913-4918
Zu & Bard, (2001) *Anal. Chem.* 73: 3960-396
U.S. Pat. No. 4,851,331
U.S. Pat. No. 5,185,243
U.S. Pat. No. 5,503,980
U.S. Pat. No. 5,573,907
U.S. Pat. No. 5,679,524
WO 94/21820
WO 96/41011
WO 97/31256

It will be understood that various details of the invention can be changed without departing from the scope of the invention. Furthermore, the foregoing description is for the purpose of illustration only, and not for the purpose of limitation.

What is claimed is:

1. A method of detecting a plurality of different target analytes comprising:
    (a) providing a conductive support comprising a single electrode, wherein said single electrode comprises an array comprising a plurality of different probes, wherein each of the plurality of different probes is attached at one of a plurality of discrete positions;
    (b) contacting the plurality of different probes with a plurality of different target analytes, wherein each of the plurality of different target analytes is selected from the group consisting of a single stranded DNA oligomer, a single stranded RNA oligomer, a peptide nucleic acid analog, double stranded DNA, an antibody, a polypeptide, a peptide, a target analyte that is reverse transcribed from a nucleic acid sequence, a target analyte comprising intact genomic DNA, a target analyte comprising fragmented genomic DNA, mRNA, a PCR product and an OLA product, further wherein each of the plurality of different target analytes comprises a nanoparticle comprising a photoelectrochemically active moiety, thereby forming a support comprising a plurality of different target analytes attached thereto;

(c) irradiating one of the plurality of discrete positions with light individually, thereby generating a photoelectric current between a photoelectrochemically active moiety and the conductive support if a target analyte is present;

(d) measuring the photoelectric current to determine the presence or the amount of a target analyte at the discrete position irradiated; and (e) repeating the irradiating and measuring steps for each of a plurality of discrete positions on the support sequentially, thereby determining the presence or the amount of each of a plurality of different target analytes.

2. The method of 1, wherein the nanoparticle comprises a material selected from the group consisting of a metal, a metal oxide, a ceramic, a semiconductor, a dendrimer and an organic polymer.

3. The method of claim 2, wherein the nanoparticle comprises a material selected from the group consisting of titanium, titanium dioxide, tin, tin oxide, silicon, silicon dioxide, iron, iron$^{III}$ oxide, silver, gold, copper, nickel, aluminum, steel, indium, indium tin oxide, fluoride-doped tin, ruthenium oxide, germanium cadmium selenide, cadmium sulfide and titanium alloy.

4. The method of claim 1, wherein the support comprises a material selected from the group consisting of titanium dioxide, tin oxide, silicon, iron$^{III}$ oxide, silver, nickel, gold, indium tin oxide, conductive polymers, metals, semiconductors and plastics coated with a conductant.

5. The method of claim 1, wherein each of the plurality of different target analytes is an oligonucleotide whose sequence is determined by surface binding or hybridization.

6. The method of claim 5, wherein each of the plurality of different target analytes further comprises a tag sequence.

7. The method of claim 1, wherein the photoelectrochemically active moiety comprises a ruthenium center.

8. The method of claim 1, wherein the light is provided by a light source selected from the group consisting of a tungsten halogen light source, a xenon arc lamp and a laser.

9. The method of claim 1, wherein the irradiating is by rastering.

10. The method of claim 1, wherein the irradiating is performed in the presence of a redox mediator.

11. The method of claim 1, wherein each of the plurality of different probes is selected from the group consisting of a single stranded DNA oligomer, a single stranded RNA oligomer, a peptide nucleic acid analog, double stranded DNA, an antibody, a polypeptide, a peptide, a target analyte that is reverse transcribed from a nucleic acid sequence, a target analyte comprising intact genomic DNA, a target analyte comprising fragmented genomic DNA, mRNA, a PCR product and an OLA product.

12. The method of claim 11, wherein each of the plurality of different probes further comprises a tag sequence.

13. The method of claim 1, further comprising passivating the support with a passivation moiety before contacting the plurality of different target analytes with the plurality of different probes under hybridization conditions.

14. The method of claim 13, wherein the passivation moiety comprises a moiety selected from the group consisting of silyl chloride, a sol gel, polyethylene glycol, a thiol, a siloxane, an organic polymer, a carboxylate and combinations thereof.

15. The method of claim 1, further comprising contacting the support with a secondary component after contacting the plurality of different target analytes with the plurality of different probes under hybridization conditions.

16. The method of claim 15, wherein the secondary component is a photoelectrochemically active moiety.

17. The method of claim 1, wherein the providing comprises contacting the plurality of different probes with the plurality of different target analytes under hybridization conditions and further wherein the nanoparticle comprises a central component and a plurality of photoelectrochemically active moieties.

18. The method of claim 17, wherein each of the plurality of different target analytes is selected from the group consisting of an mRNA sequence derived from a sample to be monitored for gene expression and a cDNA sequence derived from a sample to be monitored for gene expression.

19. The method of claim 18, wherein one of the plurality of different probes comprises a gene of interest.

20. The method of claim 18, wherein the presence of a photoelectric current is indicative of duplex formation and duplex formation is indicative of gene expression.

21. The method of claim 1, wherein one or more of the plurality of different probes comprises or is suspected to comprise a mutation to be detected, and the plurality of different probes is contacted with the plurality of different target analytes under hybridization conditions.

22. The method of claim 1, wherein the nanoparticle comprises a central component comprising gold or titanium dioxide, said central component having attached thereto a plurality of thiolated $[Ru(bpy)_3]^{2+}$ groups.

23. The method of claim 1, wherein each of the plurality of different target analytes is isolated from a cell or is chemically or enzymatically synthesized.

* * * * *